US006632618B1

(12) United States Patent
Dijke et al.

(10) Patent No.: US 6,632,618 B1
(45) Date of Patent: Oct. 14, 2003

(54) MORPHOGENIC PROTEIN-SPECIFIC CELL SURFACE RECEPTORS AND USES THEREFOR

(75) Inventors: Peter ten Dijke; Carl-Henrik Heldin, both of Uppsala (SE); Kohei Miyazono, Asaka (JP); Kuber T. Sampath, Medway, MA (US)

(73) Assignees: Curtis, Inc., Cambridge, MA (US); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/448,371

(22) Filed: Jun. 2, 1995

Related U.S. Application Data

(63) Continuation-in-part of application No. 08/236,428, filed on Apr. 29, 1994, now abandoned.

(51) Int. Cl.[7] ..................... G01N 33/566; C07K 14/71; C07K 14/51
(52) U.S. Cl. .................. 435/7.2; 435/69.1; 435/7.1; 435/194; 435/320.1; 435/325; 435/252.3; 435/254.11; 530/300; 530/350; 536/23.1; 536/23.5
(58) Field of Search ................................ 530/300, 350, 530/387.1; 435/6, 7.1, 7.2, 8, 69.1, 320.1, 325, 252.3, 254.11, 194; 436/501

(56) References Cited

U.S. PATENT DOCUMENTS

| 5,434,067 A | * | 7/1995 | Michaelis et al. | ........... 435/196 |
| 5,538,892 A | * | 7/1996 | Donahoe et al. | ......... 435/240.2 |

FOREIGN PATENT DOCUMENTS

| WO | WO 90/11366 | * 10/1990 |
| WO | WO 91/05802 | *  5/1991 |
| WO | WO93/05172 | 3/1993 |
| WO | WO93/19177 | 9/1993 |
| WO | WO94/11502 | 5/1994 |
| WO | WO95/07982 | 3/1995 |
| WO | WO95/14778 | 6/1995 |

OTHER PUBLICATIONS

Ten Dijke et al. (1993), "Activin Receptor–Like Kinases; A Novel Subclass of Cell Surface Receptors with Predicted Serine/Threonine Kinase Activity,"*Oncogene* 8:2879–2887.
Yamaji et al. (1993), "The molecular cloning of bone morphogenic protein receptors,"*Journal of Bone & Mineral Research* 8:S145.
Vukicevic et al. (1994), "Localization of Osteogenic Protein–1 (Bone Morphogenetic Protein–7) During Human Embryonic Development: High Affinity Binding to Basement Membranes,"*Bio. Chem & Biophysical Research Communications* 198:693–700.

Koenig et al. (1994), "Characterization and Cloning of a Receptor for BMP–2 and BMP–4 from NIH 3T3 Cells,"*Mol Cell Biol* 14:5961–5974.
Ten Dijke et al. (1994), "Identification of Type I Receptors for Osteogenic Protein–1 and Bone Morphogenetic Protein–4," *J. Biol Chem* 269:16985–16988.
Kawabata et al. (1995), "Cloning of a Novel Type II Serine/Threonine Kinase Receptor through Interaction with the Type I Transforming Growth Factor–β Receptor," *J. Biol Chem* 270:5625–5630.
Ausubel et al., Eds., Short Protocols in Molecular Biology, John Wiley & Sons:New York, NY, pp. 185–191, 1989.*
Strader et al., Structural basis of beta–adrenergic receptor function, FASEB J., 3: 1825–1832, 1989.*
Dijke et al., Characterization of type I receptors for transforming growth factor–beta and activin, Science, 264: 101–104, Apr. 1994.*
Sampath et al., Recombinant human osteogenic protein–1 (hOP–1) induces new bone formation in vivo with a specific activity comparagble with natural bovine osteogenic protein and stimulates osteoblast proliferation and differentiation in vitro, J. Biol. C, Oct. 1992.*
Thompson et al., Vargula hilgendorfii luciferase: a secreted reporter enzyme for monitoring gene expression in mammalian cells, Gene, 96:257–262, 1990.*
Gibbs, W., More fun than a root canal, Scientific Am., 269)5): 106, Nov. 1993.*
Cagan et al., The role of induction in cell choice and cell cycle in the developing drosophila retina, In: Molecular Basis of Morphogenesis, M. Bernfield, Ed., Wiley–Liss-:New York, NY, 109–133, 1993.*

(List continued on next page.)

OTHER PUBLICATIONS

Paralkar et al., "Identification and Characterization of Cellular Binding Proteins . . . Bone Differentiation Cascade", *Proc. Natl. Acad. Sci. USA* 88:3397–3401 (1991).

(List continued on next page.)

*Primary Examiner*—Claire M. Kaufman
(74) *Attorney, Agent, or Firm*—Ivor R. Elrifi; Mintz, Levin, Cohn, Ferris, Glowsky and Popeo, P.C.

(57) ABSTRACT

Disclosed are (1) nucleic acid sequences, amino acid sequences, homologies, structural features and various other data characterizing a morphogen cell surface receptors particularly OP-1-binding cell surface receptors ALK-2, ALK-3, and ALK-6; (2) methods for producing receptor proteins, including fragments thereof, using recombinant DNA technology; (3) methods for identifying novel morphogen receptors and their encoding DNAS; (4) methods and compositions for identifying compounds capable of modulating endogenous morphogen receptor levels; and (5) methods and compositions for identifying morphogen receptor binding analogs useful in the design of morphogen agonists and antagonists for therapeutic, diagnostic and experimental uses.

6 Claims, 3 Drawing Sheets

OTHER PUBLICATIONS

Attisano et al., "Identification of Human Activin & TGF–β... with Type II Receptors", *Cell* 75:671–680 (1993).

Bassing et al., "A Transforming Growth Factor β Type I Receptor ... Gene Expression", *Science* 263:87–89 (1994).

Inagaki et al., "Growth Inhibition by Transforming Growth Factor β Type I ... TGF–β Receptor Type II cDNA", *Proc. Natl. Acad. Sci. USA* 90:5359–5363 (1993).

Tsuchida et al., "Cloning and Characterization of a Transmembrane Serine Kinase ... Type I Receptor", *Proc. Natl. Acad. Sci. USA* 90:11242–11246 (1993).

He, et al.; "Developmental Expression of Four Novel Serine/Theronine Kinase ... Type II Receptor Family", *Develoment Dynamics* 196:133–142 (1993).

Matsuzaki et al., "A Widely Expressed Transmembrane Serine/Threonine Kinase ... Bone Morphogenic Factor", *J. Bio, Chem.* 268:12719–12722 (1993).

Estevez et al., "The daf–4 Gene Encodes a Bone Morphogenetic . . . Dauer Larva Development", *Nature* 365:644–649 (1993).

Franzen et al., "Cloning of a TGF–β Type I Receptor That Forms a Heteromeric Complex with the TGF–β Type II Receptor", *Cell* 75:681–692 (1993).

Massague, "Receptors for the TGF–β Family", *Cell* 69 : 1067–1070 (1992).

Wrana et al., "TGF–β Signals Through a Heteromeric Protein Kinase Receptor Complex", *Cell* 71:1003–1014 (1992).

Childs et al., "Identification of a Drosophila Activin Receptor", *Proc. Natl. Acad. Sci. USA* 90:9475–9479 (1993).

Mathews et al., "Cloning of a Second Type of Activin Receptor and Functional Characterization in Xenopus Embryos", *Science* 255:1702–1705 (1992).

Ebner et al., "Determination of Type I Receptor Specificity by the Type II Receptors for TGF–β or Activin", *Science* 262:900–902 (1993).

Ebner et al., "Cloning of a Type I TGF–β Receptor and Its Effect on TGF–β Binding to the Type II Receptor", *Science* 260:1344–1344 (1993).

Lin et al., "Receptors for the TGF–β Superfamily: Multiple Polypeptides and Serine/Threonine Kinases", *Cell* 3:14–25 (1993).

* cited by examiner

```
                                                          ALK-2
   ----------LPSPSMEDEKPKVNPKLYMCVGEGLSCGNE---DHC EGQQCESSLSINDGFHVY   ALK-3
QGQNLDSMLHGTGMKSDSDQKKSENGVTLAPEDTLPFLKCYCSG-HCPDBAINNTCITNGHCFAIEEDDQGETT   ALK-6
---------------PTPRPKILRCKCHH-HCPEDSVNNICSTDGYCFTMIEEDDSGMPV

-QKGCFQVYEQGKMTCKTPPSPGQ--AVECCQGDW-CNRNITAQEPTK--GKSFPGTQNFHLE               ALK-2
LASGCMK-YEGSDFQCKDSPKAQLRRTECCRTNL-CNQYIQPTLPPVVIGPFFDGSIR                    ALK-3
VTSGCLG-LEGSDFQCCRDTPIPHQRRSLECCTERNECNKDEHPTLPPLKDRDFVDGPIHHK                ALK-6
```

Fig. 2

```
                                                               ALK-2
                                                               ALK-3
                                                               ALK-6
-RKFKRRNQERLNPPDVEYGTIEGLTTNVGDSTQADTLDHSCTSGSGSGLPFLVQRTVARQTTLLECVGKGRYG
---KSISSRRRYNRDLEQD---EAFIP--VGES-LKDLLDQSQSGSGSGLPLLVQRTIAKQIQMVRQVGKGRYG
FRYKRQEARPRYSIGLEQD---ETYIP--PGES-LRDILEQSQSGSGSGLPLLVQRTAKQIQMVKQIGKGRYG

ALK-2
                                                               ALK-3
                                                               ALK-4
EVWRGSWQGENVAVKIFSSRDEKSWFRETELYNTVMLRHENILGFIASDMTSRHSISTQLWLIITHYHEMGSLYDYL
EVWMGKWRGEKVAVKVFFTTEEASWFRETEIYQTVMRHENILGFIAADIKGTGSWTQLYLIIDYHENGSLYDFL
EVWMGKWRGEKVAVKVFFTTEEASWFRETEIXQTVLMRHENILGFIAADIKGIGSWTQLYLIIDYHENGSLYDYL

ALK-2
                                                               ALK-3
                                                               ALK-6
QLTTLDTVSCLRIVLSIASGLAHLHIEIFGTQGKPAIAHRDLKSKNILVKKNGQCCIADLGLAVMHSQSTNQLDV
KCAILDTRALLKLAYSAACGLCHLHTEIYGTQGKPAIAHRDLKSKNILIKKNGSCCIADLGLAVKENSDTNEVDV
KSTLLDAKSMLKIAYSVSGLCHLHTEIFSTQGKPAIAHRDLKSKNILVKKNGTCCTADLGLAVKEIISDINEVDI

ALK-2
                                                               ALK-3
                                                               ALK-6
GNNPRVGTKRYMAPEVLDETIQVDCFEDSMKRVDIWAFGLVLWEVARRMVSNGIVEDMKPPFYDVVPNDPSFEDMR
PLNTRVGTKRYMAPEVLDESTNKNHFQPYIMADIYMSEGLIHWEMARRCITGGIVEEYQLPYYNMVPSDPSYEDMR
PPNTRVGTKRVMPPEVLDESLNRNHFQSYIMADMYSFGLILWEIARRCVSGGIVEEYQLPYHDLVPSDPSYEDMR

ALK-2
                                                               ALK-3
                                                               ALK-6
KVVGVDQQRPNIPNRWFSDPTITSLAKLMKECWYQNPSARLTALRIKKTLTKIDNSLDKLKTDC
EVVCVKRLRPIVSNRWNSDECIPAVLKLMSECWAHNPASRLTALRIKKTLTKLAKMVESQBVKI
EIVCMKKLRPSFPNRWSSDECLRQMGKLMTECWAQNPASRLTALRVKKTLAKMSESQDIKL
```

Fig. 3

SEQUENCE LISTING (1) GENERAL INFORMATION:

(iii) NUMBER OF SEQUENCES: 18

(2) INFORMATION FOR SEQ ID NO:1:

-continued

```
    (i) SEQUENCE CHARACTERISTICS:
        (A) LENGTH: 1509 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1509
        (D) OTHER INFORMATION: /product= "Human ALK1"

(xi) SEQUENCE DESCRIPTION: SEQ ID NO:1:
```

| | | | | | | | | | | | | | | | | |
|---|---|---|---|---|---|---|---|---|---|---|---|---|---|---|---|---|
| ATG | ACC | TTG | GGC | TCC | CCC | AGG | AAA | GGC | CTT | CTG | ATG | CTG | CTG | ATG | GCC | 48 |
| Met | Thr | Leu | Gly | Ser | Pro | Arg | Lys | Gly | Leu | Leu | Met | Leu | Leu | Met | Ala | |
| 1 | | | | 5 | | | | | 10 | | | | | 15 | | |
| TTG | GTG | ACC | CAG | GGA | GAC | CCT | GTG | AAG | CCG | TCT | CGG | GGC | CCG | CTG | GTG | 96 |
| Leu | Val | Thr | Gln | Gly | Asp | Pro | Val | Lys | Pro | Ser | Arg | Gly | Pro | Leu | Val | |
| | | | 20 | | | | | 25 | | | | | 30 | | | |
| ACC | TGC | ACG | TGT | GAG | AGC | CCA | CAT | TGC | AAG | GGG | CCT | ACC | TGC | CGG | GGG | 144 |
| Thr | Cys | Thr | Cys | Glu | Ser | Pro | His | Cys | Lys | Gly | Pro | Thr | Cys | Arg | Gly | |
| | | | | 35 | | | | | 40 | | | | | 45 | | |
| GCC | TGG | TGC | ACA | GTA | GTG | CTG | GTG | CGG | GAG | GAG | GGG | AGG | CAC | CCC | CAG | 192 |
| Ala | Trp | Cys | Thr | Val | Val | Leu | Val | Arg | Glu | Glu | Gly | Arg | His | Pro | Gln | |
| | 50 | | | | 55 | | | | | 60 | | | | | | |
| GAA | CAT | CGG | GGC | TGC | GGG | AAC | TTG | CAC | AGG | GAG | CTC | TGC | AGG | GGG | CGC | 240 |
| Glu | His | Arg | Gly | Cys | Gly | Asn | Leu | His | Arg | Glu | Leu | Cys | Arg | Gly | Arg | |
| 65 | | | | | 70 | | | | | 75 | | | | | 80 | |
| CCC | ACC | GAG | TTC | GTC | AAC | CAC | TAC | TGC | TGC | GAC | AGC | CAC | CTC | TGC | AAC | 288 |
| Pro | Thr | Glu | Phe | Val | Asn | His | Tyr | Cys | Cys | Asp | Ser | His | Leu | Cys | Asn | |
| | | | | 85 | | | | | 90 | | | | | 95 | | |
| CAC | AAC | GTG | TCC | CTG | GTG | CTG | GAG | GCC | ACC | CAA | CCT | CCT | TCG | GAG | CAG | 336 |
| His | Asn | Val | Ser | Leu | Val | Leu | Glu | Ala | Thr | Gln | Pro | Pro | Ser | Glu | Gln | |
| | | | 100 | | | | | 105 | | | | | 110 | | | |
| CCG | GGA | ACA | GAT | GGC | CAG | CTG | GCC | CTG | ATC | CTG | GGC | CCC | GTG | CTG | GCC | 384 |
| Pro | Gly | Thr | Asp | Gly | Gln | Leu | Ala | Leu | Ile | Leu | Gly | Pro | Val | Leu | Ala | |
| | | | | 115 | | | | | 120 | | | | | 125 | | |
| TTG | CTG | GCC | CTG | GTG | GCC | CTG | GGT | GTC | CTG | GGC | CTG | TGG | CAT | GTC | CGA | 432 |
| Leu | Leu | Ala | Leu | Val | Ala | Leu | Gly | Val | Leu | Gly | Leu | Trp | His | Val | Arg | |
| | 130 | | | | 135 | | | | | 140 | | | | | | |
| CGG | AGG | CAG | GAG | AAG | CAG | CGT | GGC | CTG | CAC | AGC | GAG | CTG | GGA | GAG | TCC | 480 |
| Arg | Arg | Gln | Glu | Lys | Gln | Arg | Gly | Leu | His | Ser | Glu | Leu | Gly | Glu | Ser | |
| 145 | | | | | 150 | | | | | 155 | | | | | 160 | |
| AGT | CTC | ATC | CTG | AAA | GCA | TCT | GAG | CAG | GGC | GAC | ACG | ATG | TTG | GGG | GAC | 528 |
| Ser | Leu | Ile | Leu | Lys | Ala | Ser | Glu | Gln | Gly | Asp | Thr | Met | Leu | Gly | Asp | |
| | | | | 165 | | | | | 170 | | | | | 175 | | |
| CTC | CTG | GAC | AGT | GAC | TGC | ACC | ACA | GGG | AGT | GGC | TCA | GGG | CTC | CCC | TTC | 576 |
| Leu | Leu | Asp | Ser | Asp | Cys | Thr | Thr | Gly | Ser | Gly | Ser | Gly | Leu | Pro | Phe | |
| | | | 180 | | | | | 185 | | | | | 190 | | | |
| CTG | GTG | CAG | AGG | ACA | GTG | GCA | CGG | CAG | GTT | GCC | TTG | GTG | GAG | TGT | GTG | 624 |
| Leu | Val | Gln | Arg | Thr | Val | Ala | Arg | Gln | Val | Ala | Leu | Val | Glu | Cys | Val | |
| | | | | 195 | | | | | 200 | | | | | 205 | | |
| GGA | AAA | GGC | CGC | TAT | GGC | GAA | GTG | TGG | CGG | GGC | TTG | TGG | CAC | GGT | GAG | 672 |
| Gly | Lys | Gly | Arg | Tyr | Gly | Glu | Val | Trp | Arg | Gly | Leu | Trp | His | Gly | Glu | |
| | | 210 | | | | | 215 | | | | | 220 | | | | |
| AGT | GTG | GCC | GTC | AAG | ATC | TTC | TCC | TCG | AGG | GAT | GAA | CAG | TCC | TGG | TTC | 720 |
| Ser | Val | Ala | Val | Lys | Ile | Phe | Ser | Ser | Arg | Asp | Glu | Gln | Ser | Trp | Phe | |
| 225 | | | | | 230 | | | | | 235 | | | | | 240 | |
| CGG | GAG | ACT | GAG | ATC | TAT | AAC | ACA | GTA | TTG | CTC | AGA | CAC | GAC | AAC | ATC | 768 |
| Arg | Glu | Thr | Glu | Ile | Tyr | Asn | Thr | Val | Leu | Leu | Arg | His | Asp | Asn | Ile | |
| | | | | 245 | | | | | 250 | | | | | 255 | | |

```
CTA GGC TTC ATC GCC TCA GAC ATG ACC TCC CGC AAC TCG AGC ACG CAG        816
Leu Gly Phe Ile Ala Ser Asp Met Thr Ser Arg Asn Ser Ser Thr Gln
            260                 265                 270

CTG TGG CTC ATC ACG CAC TAC CAC GAG CAC GGC TCC CTC TAC GAC TTT        864
Leu Trp Leu Ile Thr His Tyr His Glu His Gly Ser Leu Tyr Asp Phe
            275                 280                 285

CTG CAG AGA CAG ACG CTG GAG CCC CAT CTG GCT CTG AGG CTA GCT GTG        912
Leu Gln Arg Gln Thr Leu Glu Pro His Leu Ala Leu Arg Leu Ala Val
            290                 295                 300

TCC GCG GCA TGC GGC CTG GCG CAC CTG CAC GTG GAG ATC TTC GGT ACA        960
Ser Ala Ala Cys Gly Leu Ala His Leu His Val Glu Ile Phe Gly Thr
305                 310                 315                 320

CAG GGC AAA CCA GCC ATT GCC CAC CGC GAC TTC AAG AGC CGC AAT GTG       1008
Gln Gly Lys Pro Ala Ile Ala His Arg Asp Phe Lys Ser Arg Asn Val
            325                 330                 335

CTG GTC AAG AGC AAC CTG CAG TGT TGC ATC GCC GAC CTG GGC CTG GCT       1056
Leu Val Lys Ser Asn Leu Gln Cys Cys Ile Ala Asp Leu Gly Leu Ala
            340                 345                 350

GTG ATG CAC TCA CAG GGC AGC GAT TAC CTG GAC ATC GGC AAC AAC CCG       1104
Val Met His Ser Gln Gly Ser Asp Tyr Leu Asp Ile Gly Asn Asn Pro
            355                 360                 365

AGA GTG GGC ACC AAG CGG TAC ATG GCA CCC GAG GTG CTG GAC GAG CAG       1152
Arg Val Gly Thr Lys Arg Tyr Met Ala Pro Glu Val Leu Asp Glu Gln
            370                 375                 380

ATC CGC ACG GAC TGC TTT GAG TCC TAC AAG TGG ACT GAC ATC TGG GCC       1200
Ile Arg Thr Asp Cys Phe Glu Ser Tyr Lys Trp Thr Asp Ile Trp Ala
385                 390                 395                 400

TTT GGC CTG GTG CTG TGG GAG ATT GCC CGC CGG ACC ATC GTG AAT GGC       1248
Phe Gly Leu Val Leu Trp Glu Ile Ala Arg Arg Thr Ile Val Asn Gly
            405                 410                 415

ATC GTG GAG GAC TAT AGA CCA CCC TTC TAT GAT GTG GTG CCC AAT GAC       1296
Ile Val Glu Asp Tyr Arg Pro Pro Phe Tyr Asp Val Val Pro Asn Asp
            420                 425                 430

CCC AGC TTT GAG GAC ATG AAG AAG GTG GTG TGT GTG GAT CAG CAG ACC       1344
Pro Ser Phe Glu Asp Met Lys Lys Val Val Cys Val Asp Gln Gln Thr
            435                 440                 445

CCC ACC ATC CCT AAC CGG CTG GCT GCA GAC CCG GTC CTC TCA GGC CTA       1392
Pro Thr Ile Pro Asn Arg Leu Ala Ala Asp Pro Val Leu Ser Gly Leu
            450                 455                 460

GCT CAG ATG ATG CGG GAG TGC TGG TAC CCA AAC CCC TCT GCC CGA CTC       1440
Ala Gln Met Met Arg Glu Cys Trp Tyr Pro Asn Pro Ser Ala Arg Leu
465                 470                 475                 480

ACC GCG CTG CGG ATC AAG AAG ACA CTA CAA AAA ATT AGC AAC AGT CCA       1488
Thr Ala Leu Arg Ile Lys Lys Thr Leu Gln Lys Ile Ser Asn Ser Pro
            485                 490                 495

GAG AAG CCT AAA GTG ATT CAA                                           1509
Glu Lys Pro Lys Val Ile Gln
            500
```

(2) INFORMATION FOR SEQ ID NO:2:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Leu Gly Ser Pro Arg Lys Gly Leu Leu Met Leu Leu Met Ala
1               5                   10                  15
```

-continued

```
Leu Val Thr Gln Gly Asp Pro Val Lys Pro Ser Arg Gly Pro Leu Val
             20                  25                  30
Thr Cys Thr Cys Glu Ser Pro His Cys Lys Gly Pro Thr Cys Arg Gly
         35                  40                  45
Ala Trp Cys Thr Val Val Leu Val Arg Glu Glu Gly Arg His Pro Gln
     50                  55                  60
Glu His Arg Gly Cys Gly Asn Leu His Arg Glu Leu Cys Arg Gly Arg
 65                  70                  75                  80
Pro Thr Glu Phe Val Asn His Tyr Cys Asp Ser His Leu Cys Asn
                 85                  90                  95
His Asn Val Ser Leu Val Leu Glu Ala Thr Gln Pro Ser Glu Gln
                100                 105                 110
Pro Gly Thr Asp Gly Gln Leu Ala Leu Ile Leu Gly Pro Val Leu Ala
            115                 120                 125
Leu Leu Ala Leu Val Ala Leu Gly Val Leu Gly Leu Trp His Val Arg
        130                 135                 140
Arg Arg Gln Glu Lys Gln Arg Gly Leu His Ser Glu Leu Gly Glu Ser
145                 150                 155                 160
Ser Leu Ile Leu Lys Ala Ser Glu Gln Gly Asp Thr Met Leu Gly Asp
                165                 170                 175
Leu Leu Asp Ser Asp Cys Thr Thr Gly Ser Gly Ser Gly Leu Pro Phe
            180                 185                 190
Leu Val Gln Arg Thr Val Ala Arg Gln Val Ala Leu Val Glu Cys Val
        195                 200                 205
Gly Lys Gly Arg Tyr Gly Glu Val Trp Arg Gly Leu Trp His Gly Glu
    210                 215                 220
Ser Val Ala Val Lys Ile Phe Ser Ser Arg Asp Glu Gln Ser Trp Phe
225                 230                 235                 240
Arg Glu Thr Glu Ile Tyr Asn Thr Val Leu Leu Arg His Asp Asn Ile
                245                 250                 255
Leu Gly Phe Ile Ala Ser Asp Met Thr Ser Arg Asn Ser Ser Thr Gln
            260                 265                 270
Leu Trp Leu Ile Thr His Tyr His Glu His Gly Ser Leu Tyr Asp Phe
        275                 280                 285
Leu Gln Arg Gln Thr Leu Glu Pro His Leu Ala Leu Arg Leu Ala Val
    290                 295                 300
Ser Ala Ala Cys Gly Leu Ala His Leu His Val Glu Ile Phe Gly Thr
305                 310                 315                 320
Gln Gly Lys Pro Ala Ile Ala His Arg Asp Phe Lys Ser Arg Asn Val
                325                 330                 335
Leu Val Lys Ser Asn Leu Gln Cys Cys Ile Ala Asp Leu Gly Leu Ala
            340                 345                 350
Val Met His Ser Gln Gly Ser Asp Tyr Leu Asp Ile Gly Asn Asn Pro
        355                 360                 365
Arg Val Gly Thr Lys Arg Tyr Met Ala Pro Glu Val Leu Asp Glu Gln
    370                 375                 380
Ile Arg Thr Asp Cys Phe Glu Ser Tyr Lys Trp Thr Asp Ile Trp Ala
385                 390                 395                 400
Phe Gly Leu Val Leu Trp Glu Ile Ala Arg Arg Thr Ile Val Asn Gly
                405                 410                 415
Ile Val Glu Asp Tyr Arg Pro Pro Phe Tyr Asp Val Val Pro Asn Asp
            420                 425                 430
Pro Ser Phe Glu Asp Met Lys Lys Val Val Cys Val Asp Gln Gln Thr
```

```
                   435                 440                 445
Pro Thr Ile Pro Asn Arg Leu Ala Ala Asp Pro Val Leu Ser Gly Leu
        450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500
```

(2) INFORMATION FOR SEQ ID NO:3:

(i) SEQUENCE CHARACTERISTICS:
        (A) LENGTH: 2724 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 104..1630
        (D) OTHER INFORMATION: /product= "Human ALK2"

(xi) SEQUENCE DESCRIPTION: SEQ ID NO:3:

```
CTCCGAGTAC CCCAGTGACC AGAGTGAGAG AAGCTCTGAA CGAGGGCACG CGGCTTGAAG         60

GACTGTGGGC AGATGTGACC AAGAGCCTGC ATTAAGTTGT ACA ATG GTA GAT GGA         115
                                              Met Val Asp Gly
                                                1

GTG ATG ATT CTT CCT GTG CTT ATC ATG ATT GCT CTC CCC TCC CCT AGT         163
Val Met Ile Leu Pro Val Leu Ile Met Ile Ala Leu Pro Ser Pro Ser
  5                  10                  15                  20

ATG GAA GAT GAG AAG CCC AAG GTC AAC CCC AAA CTC TAC ATG TGT GTG         211
Met Glu Asp Glu Lys Pro Lys Val Asn Pro Lys Leu Tyr Met Cys Val
                 25                  30                  35

TGT GAA GGT CTC TCC TGC GGT AAT GAG GAC CAC TGT GAA GGC CAG CAG         259
Cys Glu Gly Leu Ser Cys Gly Asn Glu Asp His Cys Glu Gly Gln Gln
             40                  45                  50

TGC TTT TCC TCA CTG AGC ATC AAC GAT GGC TTC CAC GTC TAC CAG AAA         307
Cys Phe Ser Ser Leu Ser Ile Asn Asp Gly Phe His Val Tyr Gln Lys
         55                  60                  65

GGC TGC TTC CAG GTT TAT GAG CAG GGA AAG ATG ACC TGT AAG ACC CCG         355
Gly Cys Phe Gln Val Tyr Glu Gln Gly Lys Met Thr Cys Lys Thr Pro
     70                  75                  80

CCG TCC CCT GGC CAA GCT GTG GAG TGC TGC CAA GGG GAC TGG TGT AAC         403
Pro Ser Pro Gly Gln Ala Val Glu Cys Cys Gln Gly Asp Trp Cys Asn
 85                  90                  95                 100

AGG AAC ATC ACG GCC CAG CTG CCC ACT AAA GGA AAA TCC TTC CCT GGA         451
Arg Asn Ile Thr Ala Gln Leu Pro Thr Lys Gly Lys Ser Phe Pro Gly
                105                 110                 115

ACA CAG AAT TTC CAC TTG GAG GTT GGC CTC ATT ATT CTC TCT GTA GTG         499
Thr Gln Asn Phe His Leu Glu Val Gly Leu Ile Ile Leu Ser Val Val
            120                 125                 130

TTC GCA GTA TGT CTT TTA GCC TGC CTG CTG GGA GTT GCT CTC CGA AAA         547
Phe Ala Val Cys Leu Leu Ala Cys Leu Leu Gly Val Ala Leu Arg Lys
        135                 140                 145

TTT AAA AGG CGC AAC CAA GAA CGC CTC AAT CCC CGA GAC GTG GAG TAT         595
Phe Lys Arg Arg Asn Gln Glu Arg Leu Asn Pro Arg Asp Val Glu Tyr
    150                 155                 160

GGC ACT ATC GAA GGG CTC ATC ACC ACC AAT GTT GGA GAC AGC ACT TTA         643
```

-continued

```
Gly Thr Ile Glu Gly Leu Ile Thr Thr Asn Val Gly Asp Ser Thr Leu
165                 170                 175                 180

GCA GAT TTA TTG GAT CAT TCG TGT ACA TCA GGA AGT GGC TCT GGT CTT      691
Ala Asp Leu Leu Asp His Ser Cys Thr Ser Gly Ser Gly Ser Gly Leu
                    185                 190                 195

CCT TTT CTG GTA CAA AGA ACA GTG GCT CGC CAG ATT ACA CTG TTG GAG      739
Pro Phe Leu Val Gln Arg Thr Val Ala Arg Gln Ile Thr Leu Leu Glu
                200                 205                 210

TGT GTC GGG AAA GGC AGG TAT GGT GAG GTG TGG AGG GGC AGC TGG CAA      787
Cys Val Gly Lys Gly Arg Tyr Gly Glu Val Trp Arg Gly Ser Trp Gln
            215                 220                 225

GGG GAA AAT GTT GCC GTG AAG ATC TTC TCC TCC CGT GAT GAG AAG TCA      835
Gly Glu Asn Val Ala Val Lys Ile Phe Ser Ser Arg Asp Glu Lys Ser
230                 235                 240

TGG TTC AGG GAA ACG GAA TTG TAC AAC ACT GTG ATG CTG AGG CAT GAA      883
Trp Phe Arg Glu Thr Glu Leu Tyr Asn Thr Val Met Leu Arg His Glu
245                 250                 255                 260

AAT ATC TTA GGT TTC ATT GCT TCA GAC ATG ACA TCA AGA CAC TCC AGT      931
Asn Ile Leu Gly Phe Ile Ala Ser Asp Met Thr Ser Arg His Ser Ser
                    265                 270                 275

ACC CAG CTG TGG TTA ATT ACA CAT TAT CAT GAA ATG GGA TCG TTG TAC      979
Thr Gln Leu Trp Leu Ile Thr His Tyr His Glu Met Gly Ser Leu Tyr
                280                 285                 290

GAC TAT CTT CAG CTT ACT ACT CTG GAT ACA GTT AGC TGC CTT CGA ATA     1027
Asp Tyr Leu Gln Leu Thr Thr Leu Asp Thr Val Ser Cys Leu Arg Ile
            295                 300                 305

GTG CTG TCC ATA GCT AGT GGT CTT GCA CAT TTG CAC ATA GAG ATA TTT     1075
Val Leu Ser Ile Ala Ser Gly Leu Ala His Leu His Ile Glu Ile Phe
310                 315                 320

GGG ACC CAA GGG AAA CCA GCC ATT GCC CAT CGA GAT TTA AAG AGC AAA     1123
Gly Thr Gln Gly Lys Pro Ala Ile Ala His Arg Asp Leu Lys Ser Lys
325                 330                 335                 340

AAT ATT CTG GTT AAG AAG AAT GGA CAG TGT TGC ATA GCA GAT TTG GGC     1171
Asn Ile Leu Val Lys Lys Asn Gly Gln Cys Cys Ile Ala Asp Leu Gly
                    345                 350                 355

CTG GCA GTC ATG CAT TCC CAG AGC ACC AAT CAG CTT GAT GTG GGG AAC     1219
Leu Ala Val Met His Ser Gln Ser Thr Asn Gln Leu Asp Val Gly Asn
                360                 365                 370

AAT CCC CGT GTG GGC ACC AAG CGC TAC ATG GCC CCC GAA GTT CTA GAT     1267
Asn Pro Arg Val Gly Thr Lys Arg Tyr Met Ala Pro Glu Val Leu Asp
            375                 380                 385

GAA ACC ATC CAG GTG GAT TGT TTC GAT TCT TAT AAA AGG GTC GAT ATT     1315
Glu Thr Ile Gln Val Asp Cys Phe Asp Ser Tyr Lys Arg Val Asp Ile
390                 395                 400

TGG GCC TTT GGA CTT GTT TTG TGG GAA GTG GCC AGG CGG ATG GTG AGC     1363
Trp Ala Phe Gly Leu Val Leu Trp Glu Val Ala Arg Arg Met Val Ser
405                 410                 415                 420

AAT GGT ATA GTG GAG GAT TAC AAG CCA CCG TTC TAC GAT GTG GTT CCC     1411
Asn Gly Ile Val Glu Asp Tyr Lys Pro Pro Phe Tyr Asp Val Val Pro
                    425                 430                 435

AAT GAC CCA AGT TTT GAA GAT ATG AGG AAG GTA GTC TGT GTG GAT CAA     1459
Asn Asp Pro Ser Phe Glu Asp Met Arg Lys Val Val Cys Val Asp Gln
                440                 445                 450

CAA AGG CCA AAC ATA CCC AAC AGA TGG TTC TCA GAC CCG ACA TTA ACC     1507
Gln Arg Pro Asn Ile Pro Asn Arg Trp Phe Ser Asp Pro Thr Leu Thr
            455                 460                 465

TCT CTG GCC AAG CTA ATG AAA GAA TGC TGG TAT CAA AAT CCA TCC GCA     1555
Ser Leu Ala Lys Leu Met Lys Glu Cys Trp Tyr Gln Asn Pro Ser Ala
470                 475                 480
```

-continued

```
AGA CTC ACA GCA CTG CGT ATC AAA AAG ACT TTG ACC AAA ATT GAT AAT    1603
Arg Leu Thr Ala Leu Arg Ile Lys Lys Thr Leu Thr Lys Ile Asp Asn
485                 490                 495                 500

TCC CTC GAC AAA TTG AAA ACT GAC TGT TGACATTTTC ATAGTGTCAA           1650
Ser Leu Asp Lys Leu Lys Thr Asp Cys
            505

GAAGGAAGAT TTGACGTTGT TGTCATTGTC CAGCTGGGAC CTAATGCTGG CCTGACTGGT   1710

TGTCAGAATG GAATCCATCT GTCTCCCTCC CCAAATGGCT GCTTTGACAA GGCAGACGTC   1770

GTACCCAGCC ATGTGTTGGG GAGACATCAA AACCACCCTA ACCTCGCTCG ATGACTGTGA   1830

ACTGGGCATT TCACGAACTG TTCACACTGC AGAGACTAAT GTTGGACAGA CACTGTTGCA   1890

AAGGTAGGGA CTGGAGGAAC ACAGAGAAAT CCTAAAAGAG ATCTGGGCAT TAAGTCAGTG   1950

GCTTTGCATA GCTTTCACAA GTCTCCTAGA CACTCCCCAC GGGAAACTCA AGGAGGTGGT   2010

GAATTTTTAA TCAGCAATAT TGCCTGTGCT TCTCTTCTTT ATTGCACTAG GAATTCTTTG   2070

CATTCCTTAC TTGCACTGTT ACTCTTAATT TTAAAGACCC AACTTGCCAA AATGTTGGCT   2130

GCGTACTCCA CTGGTCTGTC TTTGATAAT AGGAATTCAA TTTGGCAAAA CAAAATGTAA    2190

TGTCAGACTT TGCTGCATTT TACACATGTG CTGATGTTTA CAATGATGCC GAACATTAGG   2250

AATTGTTTAT ACACAACTTT GCAAATTATT TATTACTTGT GCACTTAGTA GTTTTTACAA   2310

AACTGCTTTG TGCATATGTT AAAGCTTATT TTTATGTGGT CTTATGATTT TATTACAGAA   2370

ATGTTTTTAA CACTATACTC TAAAATGGAC ATTTTCTTTT ATTATCAGTT AAAATCACAT   2430

TTTAAGTGCT TCACATTTGT ATGTGTGTAG ACTGTAACTT TTTTTCAGTT CATATGCAGA   2490

ACGTATTTAG CCATTACCCA CGTGACACCA CCGAATATAT TATCGATTTA GAAGCAAAGA   2550

TTTCAGTAGA ATTTTAGTCC TGAACGCTAC GGGGAAAATG CATTTCTTC AGAATTATCC    2610

ATTACGTGCA TTTAAACTCT GCCAGAAAAA AATAACTATT TGTTTTAAT CTACTTTTTG    2670

TATTTAGTAG TTATTTGTAT AAATTAAATA AACTGTTTTC AAGTCAAAAA AAAA         2724
```

(2) INFORMATION FOR SEQ ID NO:4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125
```

```
Leu Ser Val Val Phe Ala Val Cys Leu Leu Ala Cys Leu Leu Gly Val
    130                 135                 140

Ala Leu Arg Lys Phe Lys Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

(2) INFORMATION FOR SEQ ID NO:5:

(i) SEQUENCE CHARACTERISTICS:
        (A) LENGTH: 2932 base pairs
        (B) TYPE: nucleic acid
```

(C) STRANDEDNESS: single
            (D) TOPOLOGY: linear (ii) MOLECULE TYPE: cDNA (ix) FEATURE:
            (A) NAME/KEY: CDS
            (B) LOCATION: 310..1905
            (D) OTHER INFORMATION: /product= "Human ALK3"

(xi) SEQUENCE DESCRIPTION: SEQ ID NO:5:

| | |
|---|---|
| GCTCCGCGCC GAGGGCTGGA GGATGCGTTC CCTGGGGTCC GGACTTATGA AAATATGCAT | 60 |
| CAGTTTAATA CTGTCTTGGA ATTCATGAGA TGGAAGCATA GGTCAAAGCT GTTTGGAGAA | 120 |
| AATCAGAAGT ACAGTTTTAT CTAGCCACAT CTTGGAGGAG TCGTAAGAAA GCAGTGGGAG | 180 |
| TTGAAGTCAT TGTCAAGTGC TTGCGATCTT TTACAAGAAA ATCTCACTGA ATGATAGTCA | 240 |
| TTTAAATTGG TGAAGTAGCA AGACCAATTA TTAAAGGTGA CAGTACACAG GAAACATTAC | 300 |

```
AATTGAACA ATG ACT CAG CTA TAC ATT TAC ATC AGA TTA TTG GGA GCC      348
         Met Thr Gln Leu Tyr Ile Tyr Ile Arg Leu Leu Gly Ala
           1               5                  10

TAT TTG TTC ATC ATT TCT CGT GTT CAA GGA CAG AAT CTG GAT AGT ATG    396
Tyr Leu Phe Ile Ile Ser Arg Val Gln Gly Gln Asn Leu Asp Ser Met
 15                  20                  25

CTT CAT GGC ACT GGG ATG AAA TCA GAC TCC GAC CAG AAA AAG TCA GAA    444
Leu His Gly Thr Gly Met Lys Ser Asp Ser Asp Gln Lys Lys Ser Glu
 30                  35                  40                  45

AAT GGA GTA ACC TTA GCA CCA GAG GAT ACC TTG CCT TTT TTA AAG TGC    492
Asn Gly Val Thr Leu Ala Pro Glu Asp Thr Leu Pro Phe Leu Lys Cys
                 50                  55                  60

TAT TGC TCA GGG CAC TGT CCA GAT GAT GCT ATT AAT AAC ACA TGC ATA    540
Tyr Cys Ser Gly His Cys Pro Asp Asp Ala Ile Asn Asn Thr Cys Ile
             65                  70                  75

ACT AAT GGA CAT TGC TTT GCC ATC ATA GAA GAA GAT GAC CAG GGA GAA    588
Thr Asn Gly His Cys Phe Ala Ile Ile Glu Glu Asp Asp Gln Gly Glu
         80                  85                  90

ACC ACA TTA GCT TCA GGG TGT ATG AAA TAT GAA GGA TCT GAT TTT CAG    636
Thr Thr Leu Ala Ser Gly Cys Met Lys Tyr Glu Gly Ser Asp Phe Gln
         95                 100                 105

TGC AAA GAT TCT CCA AAA GCC CAG CTA CGC CGG ACA ATA GAA TGT TGT    684
Cys Lys Asp Ser Pro Lys Ala Gln Leu Arg Arg Thr Ile Glu Cys Cys
110                 115                 120                 125

CGG ACC AAT TTA TGT AAC CAG TAT TTG CAA CCC ACA CTG CCC CCT GTT    732
Arg Thr Asn Leu Cys Asn Gln Tyr Leu Gln Pro Thr Leu Pro Pro Val
                130                 135                 140

GTC ATA GGT CCG TTT TTT GAT GGC AGC ATT CGA TGG CTG GTT TTG CTC    780
Val Ile Gly Pro Phe Phe Asp Gly Ser Ile Arg Trp Leu Val Leu Leu
            145                 150                 155

ATT TCT ATG GCT GTC TGC ATA ATT GCT ATG ATC ATC TTC TCC AGC TGC    828
Ile Ser Met Ala Val Cys Ile Ile Ala Met Ile Ile Phe Ser Ser Cys
        160                 165                 170

TTT TGT TAC AAA CAT TAT TGC AAG AGC ATC TCA AGC AGA CGT CGT TAC    876
Phe Cys Tyr Lys His Tyr Cys Lys Ser Ile Ser Ser Arg Arg Arg Tyr
175                 180                 185

AAT CGT GAT TTG GAA CAG GAT GAA GCA TTT ATT CCA GTT GGA GAA TCA    924
Asn Arg Asp Leu Glu Gln Asp Glu Ala Phe Ile Pro Val Gly Glu Ser
190                 195                 200                 205

CTA AAA GAC CTT ATT GAC CAG TCA CAA AGT TCT GGT AGT GGG TCT GGA    972
Leu Lys Asp Leu Ile Asp Gln Ser Gln Ser Ser Gly Ser Gly Ser Gly
                210                 215                 220

CTA CCT TTA TTG GTT CAG CGA ACT ATT GCC AAA CAG ATT CAG ATG GTC   1020
```

```
                    Leu Pro Leu Leu Val Gln Arg Thr Ile Ala Lys Gln Ile Gln Met Val
                            225                 230                 235

CGG CAA GTT GGT AAA GGC CGA TAT GGA GAA GTA TGG ATG GGC AAA TGG           1068
Arg Gln Val Gly Lys Gly Arg Tyr Gly Glu Val Trp Met Gly Lys Trp
        240                 245                 250

CGT GGC GAA AAA GTG GCG GTG AAA GTA TTC TTT ACC ACT GAA GAA GCC           1116
Arg Gly Glu Lys Val Ala Val Lys Val Phe Phe Thr Thr Glu Glu Ala
    255                 260                 265

AGC TGG TTT CGA GAA ACA GAA ATC TAC CAA ACT GTG CTA ATG CGC CAT           1164
Ser Trp Phe Arg Glu Thr Glu Ile Tyr Gln Thr Val Leu Met Arg His
270                 275                 280                 285

GAA AAC ATA CTT GGT TTC ATA GCG GCA GAC ATT AAA GGT ACA GGT TCC           1212
Glu Asn Ile Leu Gly Phe Ile Ala Ala Asp Ile Lys Gly Thr Gly Ser
                290                 295                 300

TGG ACT CAG CTC TAT TTG ATT ACT GAT TAC CAT GAA AAT GGA TCT CTC           1260
Trp Thr Gln Leu Tyr Leu Ile Thr Asp Tyr His Glu Asn Gly Ser Leu
            305                 310                 315

TAT GAC TTC CTG AAA TGT GCT ACA CTG GAC ACC AGA GCC CTG CTT AAA           1308
Tyr Asp Phe Leu Lys Cys Ala Thr Leu Asp Thr Arg Ala Leu Leu Lys
        320                 325                 330

TTG GCT TAT TCA GCT GCC TGT GGT CTG TGC CAC CTG CAC ACA GAA ATT           1356
Leu Ala Tyr Ser Ala Ala Cys Gly Leu Cys His Leu His Thr Glu Ile
    335                 340                 345

TAT GGC ACC CAA GGA AAG CCC GCA ATT GCT CAT CGA GAC CTA AAG AGC           1404
Tyr Gly Thr Gln Gly Lys Pro Ala Ile Ala His Arg Asp Leu Lys Ser
350                 355                 360                 365

AAA AAC ATC CTC ATC AAG AAA AAT GGG AGT TGC TGC ATT GCT GAC CTG           1452
Lys Asn Ile Leu Ile Lys Lys Asn Gly Ser Cys Cys Ile Ala Asp Leu
                370                 375                 380

GGC CTT GCT GTT AAA TTC AAC AGT GAC ACA AAT GAA GTT GAT GTG CCC           1500
Gly Leu Ala Val Lys Phe Asn Ser Asp Thr Asn Glu Val Asp Val Pro
            385                 390                 395

TTG AAT ACC AGG GTG GGC ACC AAA CGC TAC ATG GCT CCC GAA GTG CTG           1548
Leu Asn Thr Arg Val Gly Thr Lys Arg Tyr Met Ala Pro Glu Val Leu
        400                 405                 410

GAC GAA AGC CTG AAC AAA AAC CAC TTC CAG CCC TAC ATC ATG GCT GAC           1596
Asp Glu Ser Leu Asn Lys Asn His Phe Gln Pro Tyr Ile Met Ala Asp
    415                 420                 425

ATC TAC AGC TTC GGC CTA ATC ATT TGG GAG ATG GCT CGT CGT TGT ATC           1644
Ile Tyr Ser Phe Gly Leu Ile Ile Trp Glu Met Ala Arg Arg Cys Ile
430                 435                 440                 445

ACA GGA GGG ATC GTG GAA GAA TAC CAA TTG CCA TAT TAC AAC ATG GTA           1692
Thr Gly Gly Ile Val Glu Glu Tyr Gln Leu Pro Tyr Tyr Asn Met Val
                450                 455                 460

CCG AGT GAT CCG TCA TAC GAA GAT ATG CGT GAG GTT GTG TGT GTC AAA           1740
Pro Ser Asp Pro Ser Tyr Glu Asp Met Arg Glu Val Val Cys Val Lys
            465                 470                 475

CGT TTG CGG CCA ATT GTG TCT AAT CGG TGG AAC AGT GAT GAA TGT CTA           1788
Arg Leu Arg Pro Ile Val Ser Asn Arg Trp Asn Ser Asp Glu Cys Leu
        480                 485                 490

CGA GCA GTT TTG AAG CTA ATG TCA GAA TGC TGG GCC CAC AAT CCA GCC           1836
Arg Ala Val Leu Lys Leu Met Ser Glu Cys Trp Ala His Asn Pro Ala
    495                 500                 505

TCC AGA CTC ACA GCA TTG AGA ATT AAG AAG ACG CTT GCC AAG ATG GTT           1884
Ser Arg Leu Thr Ala Leu Arg Ile Lys Lys Thr Leu Ala Lys Met Val
510                 515                 520                 525

GAA TCC CAA GAT GTA AAA ATC TGATGGTTAA ACCATCGGAG GAGAAACTCT              1935
Glu Ser Gln Asp Val Lys Ile
                530
```

-continued

```
AGACTGCAAG AACTGTTTTT ACCCATGGCA TGGGTGGAAT TAGAGTGGAA TAAGGATGTT      1995

AACTTGGTTC TCAGACTCTT TCTTCACTAC GTGTTCACAG GCTGCTAATA TTAAACCTTT      2055

CAGTACTCTT ATTAGGATAC AAGCTGGGAA CTTCTAAACA CTTCATTCTT TATATATGGA      2115

CAGCTTTATT TTAAATGTGG TTTTTGATGC CTTTTTTTAA GTGGGTTTTT ATGAACTGCA      2175

TCAAGACTTC AATCCTGATT AGTGTCTCCA GTCAAGCTCT GGGTACTGAA TTGCCTGTTC      2235

ATAAAACGGT GCTTTCTGTG AAAGCCTTAA GAAGATAAAT GAGCGCAGCA GAGATGGAGA      2295

AATAGACTTT GCCTTTTACC TGAGACATTC AGTTCGTTTG TATTCTACCT TTGTAAAACA      2355

GCCTATAGAT GATGATGTGT TTGGGATACT GCTTATTTTA TGATAGTTTG TCCTGTGTCC      2415

TTAGTGATGT GTGTGTGTCT CCATGCACAT GCACGCCGGG ATTCCTCTGC TGCCATTTGA      2475

ATTAGAAGAA AATAATTTAT ATGCATGCAC AGGAAGATAT TGGTGGCCGG TGGTTTTGTG      2535

CTTTAAAAAT GCAATATCTG ACCAAGATTC GCCAATCTCA TACAAGCCAT TTACTTTGCA      2595

AGTGAGATAG CTTCCCCACC AGCTTTATTT TTAACATGA AAGCTGATGC CAAGGCCAAA       2655

AGAAGTTTAA AGCATCTGTA AATTTGGACT GTTTTCCTTC AACCACCATT TTTTTTGTGG     2715

TTATTATTTT TGTCACGGAA AGCATCCTCT CCAAAGTTGG AGCTTCTATT GCCATGAACC      2775

ATGCTTACAA AGAAAGCACT TCTTATTGAA GTGAATTCCT GCATTTGATA GCAATGTAAG      2835

TGCCTATAAC CATGTTCTAT ATTCTTTATT CTCAGTAACT TTTAAAAGGG AAGTTATTTA      2895

TATTTTGTGT ATAATGTGCT TTATTTGCAA ATCACCC                              2932
```

(2) INFORMATION FOR SEQ ID NO:6:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Gln Leu Tyr Ile Tyr Ile Arg Leu Leu Gly Ala Tyr Leu Phe
 1               5                  10                  15

Ile Ile Ser Arg Val Gln Gly Gln Asn Leu Asp Ser Met Leu His Gly
                20                  25                  30

Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Gln Gly Glu Thr Thr Leu
                85                  90                  95

Ala Ser Gly Cys Met Lys Tyr Glu Gly Ser Asp Phe Gln Cys Lys Asp
                100                 105                 110

Ser Pro Lys Ala Gln Leu Arg Arg Thr Ile Glu Cys Cys Arg Thr Asn
            115                 120                 125

Leu Cys Asn Gln Tyr Leu Gln Pro Thr Leu Pro Pro Val Val Ile Gly
        130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175
```

```
Lys His Tyr Cys Lys Ser Ile Ser Ser Arg Arg Tyr Asn Arg Asp
                180                 185                 190

Leu Glu Gln Asp Glu Ala Phe Ile Pro Val Gly Glu Ser Leu Lys Asp
            195                 200                 205

Leu Ile Asp Gln Ser Gln Ser Ser Gly Ser Gly Ser Gly Leu Pro Leu
        210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
                260                 265                 270

Arg Glu Thr Glu Ile Tyr Gln Thr Val Leu Met Arg His Glu Asn Ile
                275                 280                 285

Leu Gly Phe Ile Ala Ala Asp Ile Lys Gly Thr Gly Ser Trp Thr Gln
            290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
        370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
    530

(2) INFORMATION FOR SEQ ID NO:7:

(i) SEQUENCE CHARACTERISTICS:
        (A) LENGTH: 1952 base pairs
        (B) TYPE: nucleic acid
        (C) STRANDEDNESS: single
        (D) TOPOLOGY: linear (ii) MOLECULE TYPE: cDNA
```

(ix) FEATURE:
    (A) NAME/KEY: CDS
    (B) LOCATION: 187..1692
    (D) OTHER INFORMATION: /product= "Murine ALK6"

(xi) SEQUENCE DESCRIPTION: SEQ ID NO:7:

```
AAGCGGCGGC AGAAGTTGCC GGCGTGGTGC TCGTAGTGAG GGCGCGGAGG ACCCGGGACC      60

TGGGAAGCGG CGGCGGGTTA ACTTCGGCTG AATCACAACC ATTTGGCGCT GAGCTATGAC     120

AAGAGAGCAA ACAAAAAGTT AAAGGAGCAA CCCGGCCATA AGTGAAGAGA GAAGTTTATT     180

GATAAC ATG CTC TTA CGA AGC TCT GGA AAA TTA AAT GTG GGC ACC AAG        228
       Met Leu Leu Arg Ser Ser Gly Lys Leu Asn Val Gly Thr Lys
         1               5                  10

AAG GAG GAT GGA GAG AGT ACA GCC CCC ACC CCT CGG CCC AAG ATC CTA       276
Lys Glu Asp Gly Glu Ser Thr Ala Pro Thr Pro Arg Pro Lys Ile Leu
 15              20                  25                  30

CGT TGT AAA TGC CAC CAC CAC TGT CCG GAA GAC TCA GTC AAC AAT ATC       324
Arg Cys Lys Cys His His His Cys Pro Glu Asp Ser Val Asn Asn Ile
                 35                  40                  45

TGC AGC ACA GAT GGG TAC TGC TTC ACG ATG ATA GAA GAA GAT GAC TCT       372
Cys Ser Thr Asp Gly Tyr Cys Phe Thr Met Ile Glu Glu Asp Asp Ser
             50                  55                  60

GGA ATG CCT GTT GTC ACC TCT GGA TGT CTA GGA CTA GAA GGG TCA GAT       420
Gly Met Pro Val Val Thr Ser Gly Cys Leu Gly Leu Glu Gly Ser Asp
         65                  70                  75

TTT CAA TGT CGT GAC ACT CCC ATT CCT CAT CAA AGA AGA TCA ATT GAA       468
Phe Gln Cys Arg Asp Thr Pro Ile Pro His Gln Arg Arg Ser Ile Glu
     80                  85                  90

TGC TGC ACA GAA AGG AAT GAG TGT AAT AAA GAC CTC CAC CCC ACT CTG       516
Cys Cys Thr Glu Arg Asn Glu Cys Asn Lys Asp Leu His Pro Thr Leu
 95                 100                 105                 110

CCT CCT CTC AAG GAC AGA GAT TTT GTT GAT GGG CCC ATA CAC CAC AAG       564
Pro Pro Leu Lys Asp Arg Asp Phe Val Asp Gly Pro Ile His His Lys
                115                 120                 125

GCC TTG CTT ATC TCT GTG ACT GTC TGT AGT TTA CTC TTG GTC CTC ATT       612
Ala Leu Leu Ile Ser Val Thr Val Cys Ser Leu Leu Leu Val Leu Ile
            130                 135                 140

ATT TTA TTC TGT TAC TTC AGG TAT AAA AGA CAA GAA GCC CGA CCT CGG       660
Ile Leu Phe Cys Tyr Phe Arg Tyr Lys Arg Gln Glu Ala Arg Pro Arg
        145                 150                 155

TAC AGC ATT GGG CTG GAG CAG GAC GAG ACA TAC ATT CCT CCT GGA GAG       708
Tyr Ser Ile Gly Leu Glu Gln Asp Glu Thr Tyr Ile Pro Pro Gly Glu
160                 165                 170

TCC CTG AGA GAC TTG ATC GAG CAG TCT CAG AGC TCG GGA AGT GGA TCA       756
Ser Leu Arg Asp Leu Ile Glu Gln Ser Gln Ser Ser Gly Ser Gly Ser
175                 180                 185                 190

GGC CTC CCT CTG CTG GTC CAA AGG ACA ATA GCT AAG CAA ATT CAG ATG       804
Gly Leu Pro Leu Leu Val Gln Arg Thr Ile Ala Lys Gln Ile Gln Met
                195                 200                 205

GTG AAG CAG ATT GGA AAA GGC CGC TAT GGC GAG GTG TGG ATG GGA AAG       852
Val Lys Gln Ile Gly Lys Gly Arg Tyr Gly Glu Val Trp Met Gly Lys
            210                 215                 220

TGG CGT GGA GAA AAG GTG GCT GTG AAA GTG TTC TTC ACC ACG GAG GAA       900
Trp Arg Gly Glu Lys Val Ala Val Lys Val Phe Phe Thr Thr Glu Glu
        225                 230                 235

GCC AGC TGG TTC CGA GAG ACT GAG ATA TAT CAG ACG GTC CTG ATG CGG       948
Ala Ser Trp Phe Arg Glu Thr Glu Ile Tyr Gln Thr Val Leu Met Arg
    240                 245                 250

CAT GAG AAT ATT CTG GGG TTC ATT GCT GCA GAT ATC AAA GGG ACT GGG       996
His Glu Asn Ile Leu Gly Phe Ile Ala Ala Asp Ile Lys Gly Thr Gly
```

```
His Glu Asn Ile Leu Gly Phe Ile Ala Ala Asp Ile Lys Gly Thr Gly
255                 260                 265                 270

TCC TGG ACT CAG TTG TAC CTC ATC ACA GAC TAT CAT GAA AAC GGC TCC      1044
Ser Trp Thr Gln Leu Tyr Leu Ile Thr Asp Tyr His Glu Asn Gly Ser
            275                 280                 285

CTT TAT GAC TAT CTG AAA TCC ACC ACC TTA GAC GCA AAG TCC ATG CTG      1092
Leu Tyr Asp Tyr Leu Lys Ser Thr Thr Leu Asp Ala Lys Ser Met Leu
                290                 295                 300

AAG CTA GCC TAC TCC TCT GTC AGC GGC CTA TGC CAT TTA CAC ACG GAA      1140
Lys Leu Ala Tyr Ser Ser Val Ser Gly Leu Cys His Leu His Thr Glu
            305                 310                 315

ATC TTT AGC ACT CAA GGC AAG CCA GCA ATC GCC CAT CGA GAC TTG AAA      1188
Ile Phe Ser Thr Gln Gly Lys Pro Ala Ile Ala His Arg Asp Leu Lys
        320                 325                 330

AGT AAA AAC ATC CTG GTG AAG AAA AAT GGA ACT TGC TGC ATA GCA GAC      1236
Ser Lys Asn Ile Leu Val Lys Lys Asn Gly Thr Cys Cys Ile Ala Asp
335                 340                 345                 350

CTG GGC TTG GCT GTC AAG TTC ATT AGT GAC ACA AAT GAG GTT GAC ATC      1284
Leu Gly Leu Ala Val Lys Phe Ile Ser Asp Thr Asn Glu Val Asp Ile
                355                 360                 365

CCA CCC AAC ACC CGG GTT GGC ACC AAG CGC TAT ATG CCT CCA GAA GTG      1332
Pro Pro Asn Thr Arg Val Gly Thr Lys Arg Tyr Met Pro Pro Glu Val
            370                 375                 380

CTG GAC GAG AGC TTG AAT AGA AAC CAT TTC CAG TCC TAC ATT ATG GCT      1380
Leu Asp Glu Ser Leu Asn Arg Asn His Phe Gln Ser Tyr Ile Met Ala
        385                 390                 395

GAC ATG TAC AGC TTT GGA CTC ATC CTC TGG GAG ATT GCA AGG AGA TGT      1428
Asp Met Tyr Ser Phe Gly Leu Ile Leu Trp Glu Ile Ala Arg Arg Cys
    400                 405                 410

GTT TCT GGA GGT ATA GTG GAA GAA TAC CAG CTT CCC TAT CAC GAC CTG      1476
Val Ser Gly Gly Ile Val Glu Glu Tyr Gln Leu Pro Tyr His Asp Leu
415                 420                 425                 430

GTG CCC AGT GAC CCT TCT TAT GAG GAC ATG AGA GAA ATT GTG TGC ATG      1524
Val Pro Ser Asp Pro Ser Tyr Glu Asp Met Arg Glu Ile Val Cys Met
                435                 440                 445

AAG AAG TTA CGG CCT TCA TTC CCC AAT CGA TGG AGC AGT GAT GAG TGT      1572
Lys Lys Leu Arg Pro Ser Phe Pro Asn Arg Trp Ser Ser Asp Glu Cys
            450                 455                 460

CTC AGG CAG ATG GGG AAG CTT ATG ACA GAG TGC TGG GCG CAG AAT CCT      1620
Leu Arg Gln Met Gly Lys Leu Met Thr Glu Cys Trp Ala Gln Asn Pro
        465                 470                 475

GCC TCC AGG CTG ACG GCC CTG AGA GTT AAG AAA ACC CTT GCC AAA ATG      1668
Ala Ser Arg Leu Thr Ala Leu Arg Val Lys Lys Thr Leu Ala Lys Met
    480                 485                 490

TCA GAG TCC CAG GAC ATT AAA CTC TGACGTCAGA TACTTGTGGA CAGAGCAAGA     1722
Ser Glu Ser Gln Asp Ile Lys Leu
495                 500

ATTTCACAGA AGCATCGTTA GCCCAAGCCT TGAACGTTAG CCTACTGCCC AGTGAGTTCA    1782

GACTTTCCTG GAAGAGAGCA CGGTGGGCAG ACACAGAGGA ACCCAGAAAC ACGGATTCAT    1842

CATGGCTTTC TGAGGAGGAG AAACTGTTTG GGTAACTTGT TCAAGATATG ATGCATGTTG    1902

CTTTCTAAGA AAGCCCTGTA TTTTGAATTA CCATTTTTTT ATAAAAAAAA              1952

(2) INFORMATION FOR SEQ ID NO:8:

(i) SEQUENCE CHARACTERISTICS:
        (A) LENGTH: 502 amino acids
        (B) TYPE: amino acid
        (D) TOPOLOGY: linear
```

(ii) MOLECULE TYPE: protein (xi) SEQUENCE DESCRIPTION: SEQ ID NO:8:

```
Met Leu Leu Arg Ser Ser Gly Lys Leu Asn Val Gly Thr Lys Glu
 1               5                  10                  15

Asp Gly Glu Ser Thr Ala Pro Thr Pro Arg Pro Lys Ile Leu Arg Cys
            20                  25                  30

Lys Cys His His His Cys Pro Glu Asp Ser Val Asn Asn Ile Cys Ser
                35                  40                  45

Thr Asp Gly Tyr Cys Phe Thr Met Ile Glu Glu Asp Asp Ser Gly Met
        50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asp Arg Asp Phe Val Asp Gly Pro Ile His His Lys Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Ala Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400
```

```
Tyr Ser Phe Gly Leu Ile Leu Trp Glu Ile Ala Arg Arg Cys Val Ser
            405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Met Lys Lys
            435                 440                 445

Leu Arg Pro Ser Phe Pro Asn Arg Trp Ser Ser Asp Glu Cys Leu Arg
            450                 455                 460

Gln Met Gly Lys Leu Met Thr Glu Cys Trp Ala Gln Asn Pro Ala Ser
465                 470                 475                 480

Arg Leu Thr Ala Leu Arg Val Lys Lys Thr Leu Ala Lys Met Ser Glu
            485                 490                 495

Ser Gln Asp Ile Lys Leu
            500

(2) INFORMATION FOR SEQ ID NO:9:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..1341
        (C) IDENTIFICATION METHOD: experimental
        (D) OTHER INFORMATION: /function= "OSTEOGENIC PROTEIN"
            /product= "OP1"
            /evidence= EXPERIMENTAL
            /standard_name= "OP1"

(xi) SEQUENCE DESCRIPTION: SEQ ID NO:9:

GGTGCGGGCC CGGAGCCCGG AGCCCGGGTA GCGCGTAGAG CCGGCGCG ATG CAC GTG      57
                                                    Met His Val
                                                      1

CGC TCA CTG CGA GCT GCG GCG CCG CAC AGC TTC GTG GCG CTC TGG GCA     105
Arg Ser Leu Arg Ala Ala Ala Pro His Ser Phe Val Ala Leu Trp Ala
  5                  10                  15

CCC CTG TTC CTG CTG CGC TCC GCC CTG GCC GAC TTC AGC CTG GAC AAC     153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG     201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC     249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG     297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC     345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC     393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC     441
Pro Pro Leu Ala Ser Leu Gln Asp Ser His Phe Leu Thr Asp Ala Asp
                120                 125                 130
```

| | |
|---|---|
| ATG GTC ATG AGC TTC GTC AAC CTC GTG AAA CAT GAC AAG GAA TTC TTC<br>Met Val Met Ser Phe Val Asn Leu Val Glu His Asp Lys Glu Phe Phe<br>135                       140                       145 | 489 |
| CAC CCA CGC TAC CAC CAT CGA GAG TTC CGG TTT GAT CTT TCC AAG ATC<br>His Pro Arg Tyr His His Arg Glu Phe Arg Phe Asp Leu Ser Lys Ile<br>         150                        155                     160 | 537 |
| CCA GAA GGG GAA GCT GTC ACG GCA GCC GAA TTC CGG ATC TAC AAG GAC<br>Pro Glu Gly Glu Ala Val Thr Ala Ala Glu Phe Arg Ile Tyr Lys Asp<br>165                       170                       175 | 585 |
| TAC ATC CGG GAA CGC TTC GAC AAT GAG ACG TTC CGG ATC AGC GTT TAT<br>Tyr Ile Arg Glu Arg Phe Asp Asn Glu Thr Phe Arg Ile Ser Val Tyr<br>180                       185                       190                     195 | 633 |
| CAG GTG CTC CAG GAG CAC TTG GGC AGG GAA TCG GAT CTC TTC CTG CTC<br>Gln Val Leu Gln Glu His Leu Gly Arg Glu Ser Asp Leu Phe Leu Leu<br>                   200                       205                     210 | 681 |
| GAC AGC CGT ACC CTC TGG GCC TCG GAG GAG GGC TGG CTG GTG TTT GAC<br>Asp Ser Arg Thr Leu Trp Ala Ser Glu Glu Gly Trp Leu Val Phe Asp<br>215                       220                       225 | 729 |
| ATC ACA GCC ACC AGC AAC CAC TGG GTG GTC AAT CCG CGG CAC AAC CTG<br>Ile Thr Ala Thr Ser Asn His Trp Val Val Asn Pro Arg His Asn Leu<br>         230                       235                     240 | 777 |
| GGC CTG CAG CTC TCG GTG GAG ACG CTG GAT GGG CAG AGC ATC AAC CCC<br>Gly Leu Gln Leu Ser Val Glu Thr Leu Asp Gly Gln Ser Ile Asn Pro<br>245                       250                       255 | 825 |
| AAG TTG GCG GGC CTG ATT GGG CGG CAC GGG CCC CAG AAC AAG CAG CCC<br>Lys Leu Ala Gly Leu Ile Gly Arg His Gly Pro Gln Asn Lys Gln Pro<br>260                       265                     270                     275 | 873 |
| TTC ATG GTG GCT TTC TTC AAG GCC ACG GAG GTC CAC TTC CGC AGC ATC<br>Phe Met Val Ala Phe Phe Lys Ala Thr Glu Val His Phe Arg Ser Ile<br>                   280                       285                     290 | 921 |
| CGG TCC ACG GGG AGC AAA CAG CGC AGC CAG AAC CGC TCC AAG ACG CCC<br>Arg Ser Thr Gly Ser Lys Gln Arg Ser Gln Asn Arg Ser Lys Thr Pro<br>295                       300                       305 | 969 |
| AAG AAC CAG GAA GCC CTG CGG ATG GCC AAC GTG GCA GAG AAC AGC AGC<br>Lys Asn Gln Glu Ala Leu Arg Met Ala Asn Val Ala Glu Asn Ser Ser<br>310                       315                     320 | 1017 |
| AGC GAC CAG AGG CAG GCC TGT AAG AAG CAC GAG CTG TAT GTC AGC TTC<br>Ser Asp Gln Arg Gln Ala Cys Lys Lys His Glu Leu Tyr Val Ser Phe<br>325                       330                     335 | 1065 |
| CGA GAC CTG GGC TGG CAG GAC TGG ATC ATC GCG CCT GAA GGC TAC GCC<br>Arg Asp Leu Gly Trp Gln Asp Trp Ile Ile Ala Pro Glu Gly Tyr Ala<br>340                       345                     350                     355 | 1113 |
| GCC TAC TAC TGT GAG GGG GAG TGT GCC TTC CCT CTG AAC TCC TAC ATG<br>Ala Tyr Tyr Cys Glu Gly Glu Cys Ala Phe Pro Leu Asn Ser Tyr Met<br>                   360                       365                     370 | 1161 |
| AAC GCC ACC AAC CAC GCC ATC GTG CAG ACG CTG GTC CAC TTC ATC AAC<br>Asn Ala Thr Asn His Ala Ile Val Gln Thr Leu Val His Phe Ile Asn<br>         375                       380                     385 | 1209 |
| CCG GAA ACG GTG CCC AAG CCC TGC TGT GCG CCC ACG CAG CTC AAT GCC<br>Pro Glu Thr Val Pro Lys Pro Cys Cys Ala Pro Thr Gln Leu Asn Ala<br>390                       395                     400 | 1257 |
| ATC TCC GTC CTC TAC TTC GAT GAC AGC TCC AAC GTC ATC CTG AAG AAA<br>Ile Ser Val Leu Tyr Phe Asp Asp Ser Ser Asn Val Ile Leu Lys Lys<br>405                       410                     415 | 1305 |
| TAC AGA AAC ATG GTG GTC CGG GCC TGT GGC TGC CAC TAGCTCCTCC<br>Tyr Arg Asn Met Val Val Arg Ala Cys Gly Cys His<br>420                       425                     430 | 1351 |
| GAGAATTCAG ACCCTTTGGG CCAAGTTTT TCTGGATCCT CCATTGCTCG CCTTGGCCAG | 1411 |
| GAACCAGCAG ACCAACTGCC TTTTGTGAGA CCTTCCCCTC CCTATCCCCA ACTTTAAAGG | 1471 |

```
TGTGAGAGTA TTAGGAAACA TGAGCAGCAT ATGGCTTTTG ATCAGTTTTT CAGTGGCAGC    1531

ATCCAATGAA CAAGATCCTA CAAGCTGTGC AGGCAAAACC TAGCAGGAAA AAAAAACAAC    1591

GCATAAAGAA AAATGGCCGG GCCAGGTCAT TGGCTGGGAA GTCTCAGCCA TGCACGGACT    1651

CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAAATTGAC CCGGAAGTTC    1771

CTGTAATAAA TGTCACAATA AAACGAATGA ATGAAAAAAA AAAAAAAAA A             1822
```

(2) INFORMATION FOR SEQ ID NO:10:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:10:

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
    195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
    275                 280                 285
```

-continued

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

(2) INFORMATION FOR SEQ ID NO:11:

(i) SEQUENCE CHARACTERISTICS:
(A) LENGTH: 102 amino acids
(B) TYPE: amino acid
(C) STRANDEDNESS:
(D) TOPOLOGY: linear (ii) MOLECULE TYPE: protein (ix) FEATURE:
(A) NAME/KEY: Protein
(B) LOCATION: 1..102
(D) OTHER INFORMATION: /label= OPX
/note= "Each Xaa is independently selected from a group of one or more specified amino acids as defined in the specification"

(xi) SEQUENCE DESCRIPTION: SEQ ID NO:11:

Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100

(2) INFORMATION FOR SEQ ID NO:12:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

GCGGATCCTG TTGTGAAGGN AATATGTG                                28

(2) INFORMATION FOR SEQ ID NO:13:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GCGATCCGTC GCAGTCAAAA TTTT                                    24

(2) INFORMATION FOR SEQ ID NO:14:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

GCGGATCCGC GATATATTAA AAGCAA                                  26

(2) INFORMATION FOR SEQ ID NO:15:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

CGGAATTCTG GTGCCATATA                                         20

(2) INFORMATION FOR SEQ ID NO:16:

(i) SEQUENCE CHARACTERISTICS:
       (A) LENGTH: 6 amino acids
       (B) TYPE: amino acid
       (C) STRANDEDNESS:
       (D) TOPOLOGY: linear (ii) MOLECULE TYPE: peptide (xi) SEQUENCE DESCRIPTION: SEQ ID NO:16:

```
Gly Xaa Gly Xaa Xaa Gly
1               5

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

His Arg Asp Leu Lys Ser Lys Asn
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Gly Thr Lys Arg Tyr Met Ala Pro Glu
1               5
```

MORPHOGENIC PROTEIN-SPECIFIC CELL SURFACE RECEPTORS AND USES THEREFOR

This application is a Continuation-In-Part of Ser. No. 08/263,428 filed Apr. 29, 1994, now abandoned.

FIELD OF THE INVENTION

This invention relates generally to the field of tissue morphogenesis and more particularly to morphogenic protein-specific cell surface receptors.

BACKGROUND OF THE INVENTION

Cell differentiation is the central characteristic of tissue morphogenesis which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events which govern the stimulus for differentiation of cells is an area of intensive research. In the medical and veterinary fields, it is anticipated that the discovery of the factor or factors which control cell differentiation and tissue morphogenesis will advance significantly medicine's ability to repair and regenerate diseased or damaged mammalian tissues and organs. Particularly useful areas for human and veterinary therapeutics include reconstructive surgery and in the treatment of tissue degenerative diseases including arthritis, emphysema, osteoporosis, cardiomyopathy, cirrhosis, degenerative nerve diseases, inflammatory diseases, and cancer, and in the regeneration of tissues, organs and limbs. (In this and related applications, the terms "morphogenetic" and "morphogenic" are used interchangeably.)

A number of different factors have been isolated in recent years which appear to play a role in cell differentiation. Recently, a distinct subfamily of the "superfamily" of structurally related proteins referred to in the art as the "transforming growth factor-β (TGF-β) superfamily of proteins" have been identified as true tissue morphogens.

The members of this distinct "subfamily" of true tissue morphogenic proteins share substantial amino acid sequence homology within their morphogenetically active C-terminal domains (at least 50% identity in the C-terminal 102 amino acid sequence), including a conserved six or seven cysteine skeleton, and share the in vivo activity of inducing tissue-specific morphogenesis in a variety of organs and tissues. The proteins apparently contact and interact with progenitor cells e.g., by binding suitable cell surface molecules, predisposing or otherwise stimulating the cells to proliferate and differentiate in a morphogenetically permissive environment. These morphogenic proteins are capable of inducing the developmental cascade of cellular and molecular events that culminate in the formation of new organ-specific tissue, including any vascularization, connective tissue formation, and nerve innervation as required by the naturally occurring tissue. The proteins have been shown to induce morphogenesis of both bone cartilage and bone, as well as periodontal tissues, dentin, liver, and neural tissue, including retinal tissue.

The true tissue morphogenic proteins identified to date include proteins originally identified as bone inductive proteins. These include OP1-(osteogenic protein-1, also referred to in related applications as "OP1"), its Drosophila homolog, 60A, with which it shares 69% identity in the C-terminal "seven cysteine" domain, and the related proteins OP-2 (also referred to in related applications as "OP2") and OP-3, both of which share approximately 70–75% identity with OP-1 in the C-terminal seven cysteine domain, as well as BMP5, BMP6 and its murine homolog, Vgr-1, all of which share greater than 85% identity with OP-1 in the C-terminal seven cysteine domain, and the BMP6 Xenopus homolog, Vg1, which shares approximately 57% identity with OP-1 in the C-terminal seven cysteine domain. Other bone inductive proteins include the CBMP2 proteins (also referred to in the art as BMP2 and BMP4) and their Drosophila homolog, DPP. Another tissue morphogenic protein is GDF-1 (from mouse). See, for example, PCT documents US92/01968 and US92/07358, the disclosures of which are incorporated herein by reference.

As stated above, these true tissue morphogenic proteins are recognized in the art as a distinct subfamily of proteins different from other members of the TGF-β superfamily in that they share a high degree of sequence identity in the C-terminal domain and in that the true tissue morphogenic proteins are able to induce, on their own, the full cascade of events that result in formation of functional tissue rather than merely inducing formation of fibrotic (scar) tissue. Specifically, members of the family of morphogenic proteins are capable of all of the following in a morphogenetically permissive environment: stimulating cell proliferation and cell differentiation, and supporting the growth and maintenance of differentiated cells. The morphogenic proteins apparently may act as endocrine, paracrine or autocrine factors.

The morphogenic proteins are capable of significant species "crosstalk." That is, xenogenic (foreign species) homologs of these proteins 15 can substitute for one another in functional activity. For example, DPP and 60A, two Drosophila proteins, can substitute for their mammalian homologs, BMP2/4 and OP-1, respectively, and induce endochondral bone formation at a non-bony site in a standard rat bone formation assay. Similarly, BMP2 has been shown to rescue a dpp$^-$ mutation in Drosophila. In their native form, however, the proteins appear to be tissue-specific, each protein typically being expressed in or provided to one or only a few tissues or, alternatively, expressed only at particular times during development. For example, GDF-1 appears to be expressed primarily in neural tissue, while OP-2 appears to be expressed at relatively high levels in early (e.g., 8-day) mouse embryos. The endogenous morphogens may be synthesized by the cells on which they act, by neighboring cells, or by cells of a distant tissue, the secreted protein being transported to the cells to be acted on.

A particularly potent tissue morphogenic protein is OP-1. This protein, and its xenogenic homologs, are expressed in a number of tissues, primarily in tissues of urogenital origin, as well as in bone, mammary and salivary gland tissue, reproductive tissues, and gastrointestinal tract tissue. It is also expressed in different tissues during embryogenesis, its presence coincident with the onset of morphogenesis of that tissue.

The morphogenic protein signal transduction across a cell membrane appears to occur as a result of specific binding interaction with one or more cell surface receptors. Recent studies on cell surface receptor binding of various members of the TGF-β protein superfamily suggests that the ligands can mediate their activity by interaction with two different receptors, referred to as Type I and Type II receptors to form a hetero-complex. A cell surface bound beta-glycan also may enhance the binding interaction. The Type I and Type II receptors are both serine/threonine kinases, and share similar structures: an intracellular domain that consists essentially of the kinase, a short, extended hydrophobic sequence sufficient to span the membrane one time, and an extracellular domain characterized by a high concentration of conserved cysteines.

A number of Type II receptor sequences recently have been identified.

These include "TGF-βR II", a TGF-β Type II receptor (Lin et al. (1992) Cell 68:775–785); and numerous activin-binding receptors. See, for example, Mathews et al. (1991) Cell 65:973–982 and international patent application WO 92/20793, published Nov. 26, 1992, disclosing the "ActR II" sequence; Attisano et al., (1992) Cell 68:97–108, disclosing the "ActR-IIB" sequence; and Legerski et al. (1992) Biochem Biophys. Res. Commun 183:672–679. A different Type II receptor shown to have affinity for activin is Atr-II (Childs et al. (1993) PNAS 90:9475–9479.) Two Type II receptors have been identified in C. elegans, the daf-1 gene, (Georgi et al. (1990) Cell 61:635–25 645), having no known ligand to date, and daf-4, which has been shown to bind BMP4, but not activin or TGF-β (Estevez, et al. (1993) Nature 365:644–649.)

Ten Dijke et al. disclose the cloning of six different Type I cell surface receptors from murine and human cDNA libraries. ((1993) oncogene 8:2879–2887, and Science (1994) 264:101–104. These receptors, referenced as ALK-1 to ALK-6 ("activin receptor-like kinases"), share significant sequence identities (60–79%) and several have been identified as TGF-β binding (ALK-5) or activin binding (ALK-2, ALK-4) receptors. Xie et al. also report a Drosophila Type I receptor encoded by the sax gene (Science (1994) 263:1756–1759). The authors suggest that the protein binds DPP.

To date, the Type I receptors with which the morphogenic proteins described herein interact on the cell surface have not yet been identified, and no Type II receptor has been described as having binding affinity for OP-1 and its related sequences. Identification of these cell surface molecules, with which the morphogens interact and through which they may mediate their biological effect, is anticipated to enhance elucidation of the molecular mechanism of tissue morphogenesis and to enable development of morphogen receptor binding "analogs", e.g., compounds (which may or may not be amino acid-based macromolecules) capable of mimicking the binding affinity of a morphogen for its receptor sufficiently to act either as a receptor binding agonist or antagonist. These "analogs" have particular utility in therapeutic, diagnostic and experimental research applications.

It is an object of this invention to provide nucleic acid molecules and amino acid sequences encoding morphogenic protein binding cell surface receptors, particularly OP-1-specific binding receptor sequences. Another object is to provide methods for identifying genes in a variety of species and/or tissues, and in a variety of nucleic acid libraries encoding morphogenic protein binding receptors, particularly receptors that bind OP-1. Still another object is to provide means for designing biosynthetic receptor-binding ligand analogs, particularly OP-1 analogs, and/or for identifying natural-occurring ligand analogs, including agonists and antagonists, using the receptor molecules described herein, and analogs thereof. Another object is to provide antagonists, including soluble receptor constructs comprising the extracellular ligand-binding domain, which can modulate the availability of OP1 for receptor binding in vivo. Another object is to provide means and compositions for competing with activin-receptor and BMP2/4-receptor interactions. Yet another object is to provide means and compositions for ligand affinity purification and for diagnostic detection and quantification of ligands in a body fluid using OP1-specific cell surface receptors and ligand-binding fragments thereof. Still another object is to provides means and compositions for modulating the endogenous expression or concentration of these receptor molecules. Yet another object is to provide ligand-receptor complexes and analog sequences thereof, as well as antibodies capable of identifying and distinguishing the complex from its component proteins. Still another object is to provide means and compositions for modulating a morphogenesis in a mammal. These and other objects and features of the invention will be apparent from the description, drawings and claims which follow.

SUMMARY OF THE INVENTION

Type I and Type II cell surface receptor molecules capable of specific binding affinity with true tissue morphogenic proteins, particularly OP-1-related proteins, now have been identified. Accordingly, the invention provides ligand-receptor complexes comprising at least the ligand binding domain of these receptors and OP-1 or an OP-1 receptor-binding analog as the ligand; means for identifying and/or designing useful OP-1 receptor-binding analogs and OP-1-binding- receptor analogs; and means for modulating the tissue morphogenesis capability of a cell.

The morphogen cell surface receptors useful in this invention are referred to in the art as Type I or Type II serine/threonine kinase receptors. They share a conserved structure, including an extracellular, ligand-binding domain generally composed of about 100–130 amino acids (Type I receptors; up to about 196 amino acids for Type II receptors), a transmembrane domain sufficient to span a cellular membrane one time, and an intracellular (cytoplasmic) domain having serine/threonine kinase activity. The intact receptor is a single polypeptide chain of about 500–550 amino acids and having an apparent molecular weight of about 50–55 kDa.

Of particular utility in the methods and compositions of the invention are the Type I cell surface receptors referenced herein and in the literature as, ALK-2, ALK-3 and ALK-6, whose nucleic acids and encoded amino acid sequences are represented by the sequences in Seq. ID Nos. 3, 5 and 7 respectively, and which, as demonstrated herein below, have specific binding affinity for OP1 and OP1-related analogs. Accordingly, in one embodiment, the receptor sequences contemplated herein include OP-1 binding analogs of the ALK-2, ALK-3 and ALK-6 proteins described herein.

As used herein, ligand-receptor binding specificity is understood to mean a specific, saturable noncovalent interaction between the ligand and the receptor, and which is subject to competitive inhibition by a suitable competitor molecule. Preferred binding affinities (defined as the amount of ligand required to fill one-half (50%) of available receptor binding sites) are described herein by dissociation constant (Kd). In one embodiment, preferred binding affinities of the ligand-receptor complexes described herein have a Kd of less than $10^{-7}M$, preferably less than $5\times10^{-7}M$, more preferably less than $10^{-8}M$. In another preferred embodiment, the receptor molecules have little or no substantial binding affinity for TGF-β.

As used herein, an "OP1-specific receptor analog" is understood to mean a sequence variant of the ALK-2, ALK-3 or ALK-6 sequences which shares at least 40%, preferably at least 45%, and most preferably at least 50%, amino acid identity in the extracellular ligand binding domain with the sequence defined by residues 23–122 of Seq. ID No. 7 (ALK-6), and which has substantially the same binding affinity for OP1 as ALK-2, ALK-3 or ALK-6. ALK-6 and ALK-3 share 46% amino acid sequence identity in their ligand binding domains. Accordingly, in one preferred embodiment, the OP1-specific receptor analogs share at least 46% amino acid sequence identity with the extracellular, ligand binding domains of ALK-6 or ALK-3.

As will be appreciated by those having ordinary skill in the art, OP1-specific receptor analogs also can have binding affinity for other, related morphogenic proteins. As used herein, an OP1-specific receptor analog is understood to have substantially the same binding affinity for OP-1 as ALK-2, ALK-3 or ALK-6 if it can be competed successfully for OP-1 binding in a standard competition assay with a known OP-1 binding receptor, e.g., with ALK-2, ALK-3 or ALK-6. In one preferred embodiment, OP1-specific receptor analogs have a binding affinity for OP-1 defined by a dissociation constant of less than about $10^{-7}$ M, preferably less than about $5\times10^{-7}$M or $10^{-8}$ M. It is anticipated however, that analogs having lower binding affinities, e.g., on the order of $10^{-6}$M also will be useful. For example, such analogs may be provided to an animal to modulate availability of serum-soluble OP1 for receptor binding in vivo. Similarly, where tight binding interaction is desired, for example as part of a cancer therapy wherein the analog acts as a ligand-receptor antagonist, preferred binding affinities may be on the order of $5\times10^{-8}$M.

In another embodiment, the OP-1 binding receptor analogs contemplated by the invention include proteins encoded by nucleic acids which hybridize with the DNA sequence encoding the extracellular, ligand binding domain of ALK-2, ALK-3 or ALK-6 under stringent hybridization conditions, and which have substantially the same OP-1 binding affinity as ALK-2, ALK-3 or ALK-6. As used herein, stringent hybridization conditions are as defined in the art, (see, for example, *Molecular Cloning: A Laboratory Manual*, Maniatis et al., eds. 2d.ed., Cold Spring Harbor Press, Cold Spring Harbor, 1989.) An exemplary set of conditions is defined as: hybridization in 40% formamide, 5×SSPE, 5×Denhardt's Solution, and 0.1% SDS at 37° C. overnight, and washing in 0.1×SSPE, 0.1% SDS at 50° C.

In still another embodiment, the OP-1 binding receptor analogs contemplated by the invention include part or all of a serine/threonine kinase receptor encoded by a nucleic acid that can be amplified with one or more primers derived from ALK-1 (Seq. ID No. 1), ALK-2, ALK-3 or ALK-6 sequence in a standard PCR (polymerase chain reaction) amplification scheme. In particular, a primer or, most preferably, a pair of primers represented by any of the sequences of SEQ ID Nos. 12–15 are envisioned to be particularly useful. Use of primer pairs (e.g., SEQ. ID No. 12/15; 13/15; 14/15) are described in WO94/11502 (PCT/GB93/02367).

Useful OP1-specific receptor analogs include xenogenic (foreign species) homologs of the murine and human ALK sequences described herein, including those obtained from other mammalian species, as well as other, eukaryotic, non-mammalian xenogenic homologs. Also contemplated are biosynthetic constructs and naturally-occurring sequence variants of ALK-2, ALK-3 and ALK-6, provided these molecules, in all cases, share the appropriate identity in the ligand binding domain, and bind OP-1 specifically as defined herein. In one embodiment, sequence variants include receptor analogs which have substantially the same binding affinity for OP1 as ALK-2, ALK-3 or ALK-6 and which are recognized by an antibody having binding specificity for ALK-2, ALK-3 or ALK-6.

In another embodiment the receptors and OP-1 binding receptor analogs contemplated herein provide the means by which a morphogen, e.g., OP-1, can mediate a cellular response. In one embodiment these receptors include ALK-2, ALK-3, or ALK-6, or sequence variants or OP-1 binding analogs thereof. In another embodiment, ALK-1, including sequence variants thereof is contemplated to participate in an OP-1 mediated cellular response.

OP1-specific receptor analogs may be used as OP1 antagonists. For example, a soluble form of a receptor, e.g., consisting essentially of only the extracellular ligand-binding domain, may be provided systemically to a mammal to bind to soluble ligand, effectively competing with ligand binding to a cell surface receptor, thereby modulating (reducing) the availability of free ligand in vivo for cell surface binding.

The true tissue morphogenic proteins contemplated as useful receptor ligands in the invention include OP-1 and OP-1 receptor-binding analogs. As used herein, an "OP-1 analog" or "OP-1 receptor-binding analog" is understood to include all molecules able to functionally substitute for OP-1 in Type I receptor binding, e.g., are able to successfully compete with OP-1 for receptor binding in a standard competition assay. In one embodiment, useful OP-1 receptor-binding analogs include molecules whose binding affinity is defined by a dissociation constant of less than about $5\times10^{-6}$M, preferably less than about $10^{-7}$M or $5\times10^{-7}$M. As for the OP-specific receptor analogs above, both stronger and weaker binding affinities are contemplated to be useful in particular applications. In one preferred embodiment, these receptor-binding OP-1 analogs also bind OP-1 specific Type II serine/kinase receptors.

The OP-1 analogs contemplated herein, all of which mimic the binding activity of OP-1 or an OP-1-related protein sufficiently to act as a substitute for OP-1 in receptor binding, can act as OP-1 agonists, capable of mimicking OP-1 both in receptor binding and in inducing a transmembrane effect e.g., inducing threonine or serine-specific phosphorylation following binding. Alternatively, the OP-1 analog can act as an OP-1 antagonist, capable of mimicking OP-1 in receptor binding only, but unable to induce a transmembrane effect, thereby blocking the natural ligand from interacting with its receptor, for example. Useful applications for antagonists include their use as therapeutics to modulate uncontrolled differentiated tissue growth, such as occurs in malignant transformations such as in osteosarcomas or Paget's disease.

OP-1 analogs contemplated by the invention can be amino acid-based, e.g., sequence variants of OP-1, or antibody-derived sequences capable of functionally mimicking OP-1 binding to an OP-1-specific receptor. Examples of such antibodies may include anti-idiotypic antibodies. In a specific embodiment, the anti-idiotypic antibody mimics OP1 both in receptor binding and in ability to induce a transmembrane effect. Alternatively, the OP-1 analogs can be composed in part or in whole of other chemical structures, e.g., the analogs can be comprised in part or in whole of nonproteinaceous molecules. In addition, the OP-1 analogs contemplated can be naturally sourced or synthetically produced.

As used herein, OP-1 related sequences include sequences sharing at least 60%, preferably greater than 65% or even 70% identity with the C-terminal 102 amino acid sequence of OP-1 as defined in Seq ID NO.7, and which are able to substitute for OP-1 in ligand binding to ALK-2, ALK-3 or ALK-6, (e.g., able to compete successfully with OP-1 for binding to one or more of these receptors.) OP-1 related sequences contemplated by the invention include xenogenic homologs (e.g., the Drosophila homolog 60A), and the related sequences referenced herein and in the literature as OP-2, OP-3, BMP5, BMP6 (and its xenogenic homolog Vgr-1.) OP-1 related sequences also include sequence variants encoded by a nucleic acid which hybridizes with a DNA sequence encoding a protein comprising the C-terminal 102 amino acids of SEQ ID NO:10 under stringent hybridization conditions and which can substitute for OP-1 in an OP1-receptor binding assay. In another embodiment, an OP-1 sequence variant includes a protein which can substitute for OP-1 in a ligand-receptor binding assay and which is recognized by an antibody having binding specificity for OP1.

As used herein, "amino acid sequence homology" is understood to mean amino acid sequence similarity, and homologous sequences sharing identical or similar amino acids, where similar amino acids are conserved amino acids as defined by Dayoff et al., *Atlas of Protein Sequence and Structure*; vol.5, Suppl.3, pp.345–362 (M.O. Dayoff, ed., Nat'l BioMed. Research Fdn., Washington D.C. 1978.) Thus, a candidate sequence sharing 60% amino acid homology with a reference sequence requires that, following alignment of the candidate sequence with the reference sequence, 60% of the amino acids in the candidate sequence are identical to the corresponding amino acid in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all receptor homologies and identities calculated use ALK-6 as the reference sequence, with the extracellular domain reference sequence constituting residues 23–122 of SEQ ID NO: 8 and the intracellular serine/threonine kinase domain reference sequence constituting residues 206–495 of SEQ ID NO:8. Similarly, all OP-1 related protein homologies and identities use OP-1 as the reference sequence, with the C-terminal 102 amino acids described in Seq. ID No. constituting the seven cysteine domain.

Also as used herein, sequences are aligned for homology and identity calculations as follows: Sequences are aligned by eye to maximize sequence identity. Where receptor amino acid extracellular domain sequences are compared, the alignment first maximizes alignment of the cysteines present in the two sequences, then modifies the alignment as necessary to maximize amino acid identity and similarity between the two sequences. Where amino acid intracellular domain sequences are compared, sequences are aligned to maximize alignment of conserved amino acids in the kinase domain, where conserved amino acids are those identified by boxes in FIG. 3. The alignment then is modified as necessary to maximize amino acid identity and similarity. In all cases, internal gaps and amino acid insertions in the candidate sequence as aligned are ignored when making the homology/identity calculation. Exemplary alignments are illustrated in FIGS. 2 and 3 where the amino acid sequences for the extracellular and intracellular domains, respectively are presented in single letter format. In the figures "gaps" created by sequence alignment are indicated by dashes.

In one aspect, the invention contemplates isolated ligand-receptor complexes comprising OP-1 or an OP-1 analog as the ligand in specific binding interaction with an OP-1 binding Type I receptor or receptor analog, as defined herein. In another aspect, the invention contemplates the ligand-receptor complex comprises part or all of an OP-1 binding Type II receptor. Type II receptors contemplated to be useful include Type II receptors defined in the literature (referenced hereinabove) as having binding specificity for activin or a bone morphogenic protein such as BMP-4. Such Type II receptors include daf4, ActRII and AtrII. In still another aspect, the ligand-receptor complex comprises both a Type I and a Type II receptor and OP-1, or an OP1 analog as the ligand. In all complexes, the bound receptor can comprise just the extracellular, ligand binding domain, or can also include part or all of the transmembrane sequence, and/or the intracellular kinase domain. Similarly, the OP-1 ligand may comprise just the receptor binding sequence, longer sequences, including the mature dimeric species or any soluble form of the protein or protein analog.

The OP-1 and OP-1 analogs described herein can interact specifically with Type I and Type II receptors also known to interact with other morphogenic proteins (e.g., BMP2/BMP4) and activin. Thus invention also contemplates the use of OP-1 and OP-1 receptor-binding analogs as competitors of specific BMP-receptor and activin-receptor interactions. As will be appreciated by those having ordinary skill in the art, these binding competitors may act as either agonists or antagonists (e.g., to inhibit an activin or BMP-mediated cellular response).

In another aspect, the invention contemplates binding partners having specific binding affinity for an epitope on the ligand-receptor complex. In a preferred embodiment, the binding partner can discriminate between the complex and the uncomplexed ligand or receptor. In another embodiment, the binding partner has little or no substantial binding affinity for the uncomplexed ligand or receptor. In another preferred embodiment, the binding partner is a binding protein, more preferably an antibody. These antibodies may be monoclonal or polyclonal, may be intact molecules or fragments thereof (e.g., Fab, Fab', (Fab)'$_2$), or may be biosynthetic derivatives, including, but not limited to, for example, monoclonal fragments, such as single chain F$_v$ fragments, referred to in the literature as sF$_v$s, BABs and SCAs, and chimeric monoclonals, in which portions of the monoclonals are humanized (excluding those portions involved in antigen recognition (e.g., complementarity determining regions, "CDRs".) See, for example, U.S. Pat. Nos. 5,091,513 and 5,132,405, the disclosures of which are incorporated herein by reference. Biosynthetic chimeras, fragments and other antibody derivatives may be synthesized using standard recombinant DNA methodology and/or automated chemical nucleic acid synthesis methodology well described in the art and as described below.

In still another aspect, the invention provides molecules useful in the design and/or identification of receptor-binding morphogenic protein analogs as described below, as well as kits and methods, e,g., screening assays, for identifying these analogs. The molecules useful in these assays can include part or all of the receptor sequence of SEQ ID NO. 3, 5 or 7, including amino acid sequence variants and OP-1 binding analogs and amino acid sequence variants thereof.

As described above, sequence variants are contemplated to have substantially the same binding affinity for OP-1 as the receptors represented by the sequences in SEQ. ID NOS: 4–8 OP-1 binding receptor analogs include other, known or novel Type I or Type II serine/threonine kinase receptors having binding affinity and specificity for OP-1 as defined herein and which (1) share at least 40% amino acid identity with residues 23–122 of SIQ ID NO:8 (2) are encoded by a nucleic acid that hybridizes under stringent conditions with a nucleic acid comprising the sequence defined by nucleotides 256–552 of Seq ID No. 7; or (3) are encoded by a nucleic acid obtainable by amplification with one or more primer sequences defined by Seq. ID Nos. 12–15. Currently preferred for the assays of the invention are receptor sequences comprising at least the sequence which defines the extracellular, ligand binding domains of these proteins. The kits and assays may include just Type I receptors or both Type I and Type II receptors. Similarly, the kits and screening assays can be used in the design and/or identification of OP1-specific receptor analogs. The OP-1 receptor-binding analogs and OP-1-binding receptor analogs thus identified then can be produced in reasonable quantities using standard recombinant expression or chemical synthesis technology well known and characterized in the art. Alternatively, promising candidates can be modified using standard biological or chemical methodologies to, for example, enhance the binding affinity of the candidate analog as described in Example 10, below, and the preferred candidate derivative then produced in quantity.

In still another aspect, the receptor and/or OP1-specific receptor analogs can be used in standard methodologies for affinity purifying and/or quantifying OP1 and OP1 analogs. For example, the receptor's ligand binding domain first may be immobilized on a surface of a well or a chromatographic column; ligand in a sample fluid then may be provided to the receptor under conditions to allow specific binding; non-specific binding molecules then removed, e.g., by washing, and the bound ligand then selectively isolated and/or quantitated. Similarly, OP-1 and OP1 analogs can be used for affinity purifying and/or quantifying OP1-specific receptors and receptor analogs. In one embodiment, the method is useful in kits and assays for diagnostic purposes which detect the presence and/or concentration of OP1 protein or related morphogen in a body fluid sample including, without limitation, serum, peritoneal fluid, spinal fluid, and breast exudate. The kits and assays also can be used for detecting and/or quantitating OP-1-specific receptors in a sample.

In still another aspect the invention comprises OP1-specific receptors and OP-1-binding receptor analogs useful in screening assays to identify organs, tissues and cell lines which express OP-1 specific receptors. These cells then can be used in screening assays to identify ligands that modulate endogenous morphogen receptor expression levels, including the density of receptors expressed on a cell surface. Useful assay methodologies may be modeled on those described in PCT US92/07359, and as described below.

The invention thus relates to compositions and methods for the use of morphogen-specific receptor sequences in diagnostic, therapeutic and experimental procedures. Active receptors useful in the compositions and methods of this invention can include truncated or full length forms, as well as forms having varying glycosylation patterns. Active receptors useful in the invention also include chimeric constructs as described below. Active OP1-specific receptors/analogs can be expressed from intact or truncated genomic or cDNA, or from synthetic DNAs in procaryotic or eucaryotic host cells, and purified, cleaved, refolded and oxidized as necessary to form active molecules. Useful host cells include prokaryotes, including *E. coli* and *B. subtilis*, and eukaryotic cells, including mammalian cells, such as fibroblast 3T3 cells, CHO, COS, melanoma or BSC cells, Hela and other human cells, the insect/baculovirus system, as well as yeast and other microbial host cell systems.

Thus, in view of this disclosure, skilled genetic engineers now can, for example, identify and produce OP1-specific cell surface receptors or analogs thereof; create and perform assays for screening candidate OP1 receptor-binding analogs and evaluate promising candidates and their progency in therapeutic regimes and preclinical studies; modulate the availability of endogenous morphogen for cell surface interactions; modulate endogenous morphogen-specific cell surface receptor levels; elucidate the signal transduction pathway induced by morphogen-cell surface receptor binding; and modulate tissue morphogenesis in vivo.

BRIEF DESCRIPTION OF THE DRAWINGS

FIG. 2 is a homology alignment of the extracellular domains of ALK-2 (SEQ ID NO:4), ALK-3 (SEQ ID NO:6), and ALK-6 (SEQ ID NO:8), aligned to maximize amino acid identity, wherein conserved amino acids are identified by boxes and conserved cysteines are indicated by asterisks; and FIG. 3 is a homology alignment of the intracellular domain of ALK-2 (SEQ ID NO:4), ALK-3 (SEQ ID NO:6) and ALK-6 (SEQ ID NO:8), aligned to maximize amino acid identity, wherein conserved amino acids are boxed and the serine/threonine kinase domain is indicated by arrows.

DETAILED DESCRIPTION

Figure 1:
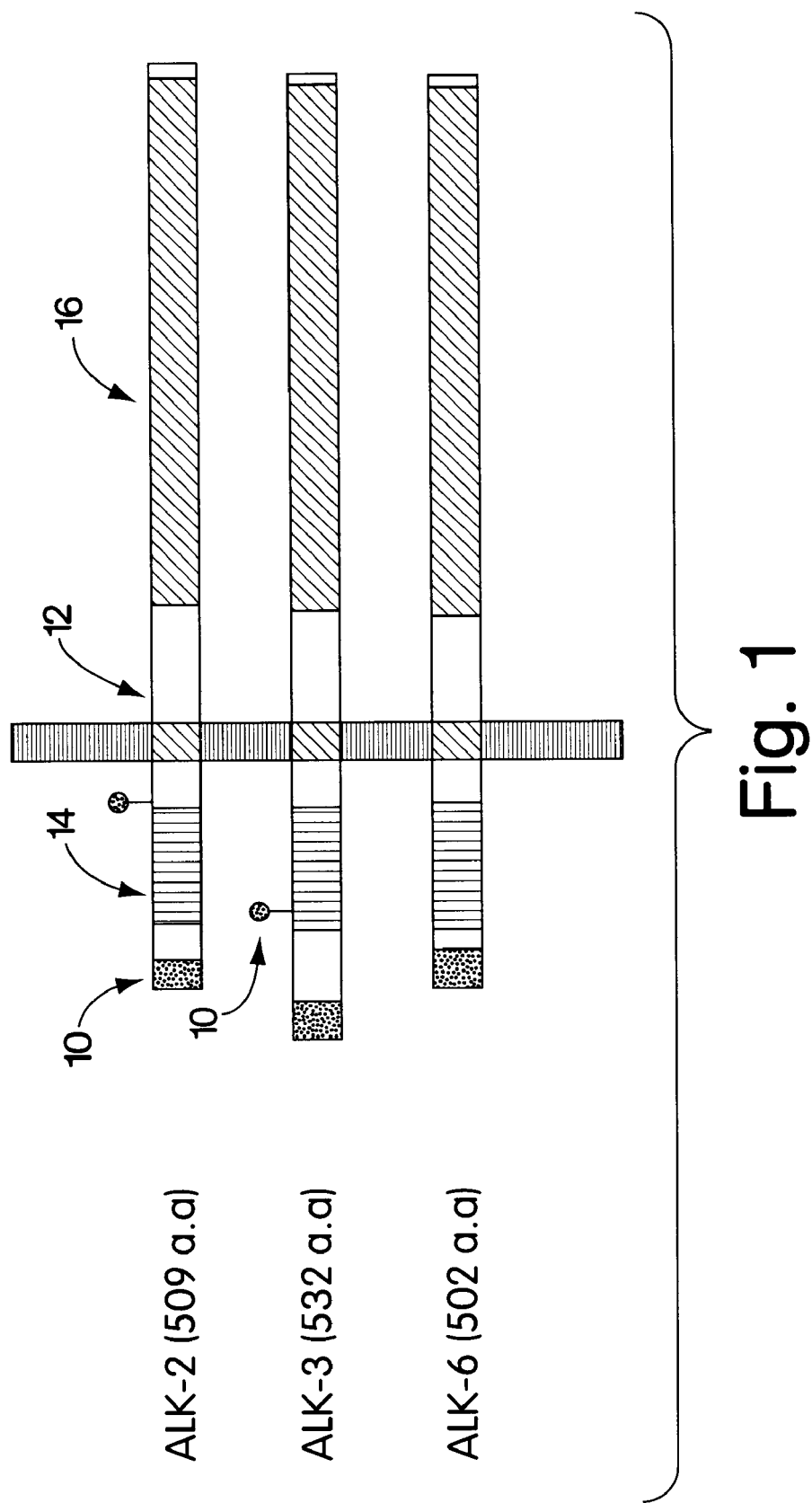
FIG. 1 is a schematic representation of the encoded ALK-2, ALK-3, ALK-6 amino acid sequences, showing the signal sequence 10, the transmembrane domain 12, the extracellular ligand binding domain 14, and the intracellular serine/threonine kinase domain 16.

Disclosed herein are Type I and Type II receptors having binding specificity for true tissue morphogenic proteins, particularly OP-1 and OP1-related proteins. It further has been determined that OP1 binds to a broader range of receptors than other known tissue morphogens or TGF-β family members. The Type I receptors disclosed herein, can be used together with OP-1 and OP1 analogs for therapeutic, diagnostic and experimental uses as described herein below. Moreover, soluble forms of the OP-1 binding receptor proteins, e.g., forms consisting essentially of the extracellular domain or a fragment thereof sufficient to bind OP-1 with specificity, can be used as a soluble therapeutic morphogen antagonist, as described below.

Following this disclosure, related OP-1 specific receptors are available, as are high and medium flux screening assays for identifying OP1 analogs and OP1-specific receptor analogs. These analogs can be naturally occurring molecules, or they can be designed and biosynthetically created using a rational drug design and an established structure/function analysis. The analogs can be amino acid-based or can be composed in part or whole of non-proteinaceous synthetic organic molecules. Useful analogs also can include antibodies, preferably monoclonal antibodies (including fragments thereof, e.g., Fab, Fab', and (Fab)'$_2$), or synthetic derivatives thereof, such as monoclonal single chain F$_v$, fragments known in the art as sF$_v$s, BABs, and SCAs (see below), and bispecific antibodies or derivatives thereof. When these antibodies mimic the binding activity of OP-1 to a cell surface receptor without inducing the biological response OP-1 does upon binding, the antibody can compete for OP-1 binding and act as an antagonist. These antibodies or derivatives thereof also can mimic OP-1 both in receptor binding and signal transduction, in which case the antibody acts as an OP-1 agonist. The antibodies and derivatives also can be used for inducing the morphogenic cellular response by crosslinking receptors to morphogenic proteins, particularly OP-1 and OP1-related proteins to form either homo- or hetero-complexes of the Type I and Type II receptors.

The OP1-binding receptor sequences described herein (ALK2, ALK3, ALK6) also can be used to create chimeric sequences, wherein, for example, part or all of either the extracellular domain or the intracellular domain is a non-ALK sequence or is created from two or more ALK sequences. These chimeric receptors can be synthesized using standard recombinant DNA methodology and/or automated chemical nucleic acid synthesis methodology well described in the art and as disclosed below. Chimerics can be used, for example, in OP-1 analog assays, wherein the OP-1 binding extracellular domain is coupled to a non-ALK intracellular domain that is well characterized and/or readily detectable as a second messenger response system, as described below. Chimerics also can be used, for example, in high flux OP-1 analogs screens and as part of purification protocols, wherein a soluble ligand binding domain of an OP1-specific receptor is immobilized onto a support e.g., by covalent or non-covalent interactions, with a chromatographic matrix or the well surface of a 96-well plate. When immobilized onto a chromatographic matrix surface, the receptor fragment can be used in a protocol to isolate OP-1 or OP1 analogs. When immobilized on a well surface the receptor fragment is particularly useful in a screening assay to identify receptor-binding OP1 analogs in a standard competition assay.

The true tissue morphogenic proteins contemplated to be useful in the methods and compositions of the invention include forms having varying glycosylation patterns and varying N-termini. The proteins can be naturally occurring or biosynthetically derived, and can be produced by expression of recombinant DNA in prokaryotic or eukaryotic host cells. The proteins are active as a single species (e.g., as homodimers), or combined as a mixed species. Useful sequences and eucaryotic and procaryotic expression systems are well described in the art. See, for example, U.S. Pat. Nos. 5,061,911 and 5,266,683 for useful expression systems.

Particularly contemplated herein are OP-1 and OP1-related sequences. Useful OP-1 sequences are recited in U.S. Pat Nos. 5,011,691; 5,018,753 and 5,266,683; in Ozkaynak et al. (1990) *EMBO J* 9:2085–2093; and Sampath et al. (1993) *PNAS* 90: 6004–6008. OP-1 related sequences include xenogenic homologs, e.g.; 60A, from Drosophila, Wharton et al. (1991) *PNAS* 88:9214–9218; and proteins sharing greater than 60% identity with OP-1 in the C-terminal seven cysteine domain, preferably at least 65% identity. Examples of OP-1 related sequences include BMP5, BMP6 (and its species homolog Vgr-1, Lyons et al. (1989) *PNAS* 86:4554–4558), Celeste, et al. (1990) *PNAS* 87:9843–9847 and PCT international application WO93/00432; OP-2 (Ozkaynak et al. (1992) *J.Eiol. Chem.* 267:13198–13205) and OP-3 (PCT international application WO94/06447). As will be appreciated by those having ordinary skill in the art, chimeric constructs readily can be created using standard molecular biology and mutagenesis techniques combining various portions of different morphogenic protein sequences to create a novel sequence, and these forms of the protein also are contemplated herein.

A particularly preferred embodiment of the proteins contemplated by the invention includes proteins whose amino acid sequence in the cysteine-rich C-terminal domain has greater than 60% identity, and preferably greater than 65% identity with the amino acid sequence of OPS (OP-1 sequence defining the C-terminal conserved six cysteines, e.g., residues 335–431 of SEQ ID NO:10).

In another preferred aspect, the invention contemplates osteogenic proteins comprising species of polypeptide chains having the generic amino acid sequence herein referred to as "OPX" which accommodates the homologies between the various identified species of the osteogenic OP-4 and OP-2 proteins, and which is described by the amino acid sequence presented below and in SEQ ID NO:12.

```
Cys Xaa Xaa His Glu Leu Tyr Val Ser Phe
 1            5                      10

Xaa Asp Leu Gly Trp Xaa ASP Trp Xaa Ile
               15                   20

Ala Pro Xaa Gly Tyr Xaa Ala Tyr Tyr Cys
               25                   30

Glu Gly Glu Cys Xaa Phe Pro Leu Xaa Ser
               35                   40

Xaa Met Asn Ala Thr Asn His Ala Ile Xaa
               45                   50

Gln Xaa Leu Val His Xaa Xaa Xaa Pro Xaa
               55                   60

Xaa Val Pro Lys Xaa Cys Cys Ala Pro Thr
               65                   70

Xaa Leu Xaa Ala Xaa Ser Val Leu Tyr Xaa
               75                   80

Asp Xaa Ser Xaa Asn Val Ile Leu Xaa Lys
               85                   90

Xaa Arg Asn Met Val Val Xaa Ala Cys Gly
               95                  100

Cys His,
``` and wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred aspect, the invention contemplates osteogenic proteins encoded by nucleic acids which hybridize to DNA or RNA sequences encoding the C-terminal seven cysteine domain of OP-1 or OP-2 under stringent hybridization conditions.

A brief description of the various terms of OP-1 useful in the invention is described below:

OP-L—Refers generically to the family of osteogenically active proteins produced by expression of part or all of the hOP1 gene. Also referred to in related applications as "OP-1" and "OP-1".

OP-L-PP—Amino acid sequence of human OP-1 protein (prepro form), SEQ ID NO.10, residues 1–431. Also referred to in related applications as "OP1-PP" and "OPP".

OP-L18Ser—Amino acid sequence of mature human OP1 protein, SEQ ID NO:10, residues 293–431. N-terminal amino acid is serine. Originally identified as migrating at 18 kDa on SDS-PAGE in COS cells. Depending on protein glycosylation pattern in different host cells, also migrates at 23 kDa, 19 kDa and 17 kDa on SDS-PAGE. Also referred to in related applications as "OP1-18."

OP1-16Ser; OP1-16Ala; OP1-16 Met; OP1-16 leu; OP1-16Val-N-terminally truncated mature human OP1 protein species defined, respectively, by residues 300–431; 316–431; 315–431; 313–431 and 318–431.

OPS—Amino acid sequence defining the C-terminal six cysteine domain, residues 335–431 of SEQ ID NO:10.

OP7—Amino acid sequence defining the C-terminal seven cysteine domain, residues 330–431 of SEQ ID NO:10.

Soluble form OP1—mature dimeric OP-1 species having one or, preferably two copies of pro domain, e.g., at least residues 158–292 of SEQ ID NO:10 preferably residues 48–292 or 30–292, non-covalently complexed with the dimer.

The cloning procedure for obtaining OP1-binding ALK nucleic acid sequences, means for expressing receptor sequences, as well as other material aspects concerning the nature and utility of these sequences, including how to make and how to use the subject matter claimed, will be further understood from the following, which constitutes the best mode currently contemplated for practicing the invention.

EXAMPLE 1

IDENTIFICATION OF ALK-1, ALK-2, ALK-3 and ALK-6

The cloning and characterization of ALK-1, -2, -3, and -6 receptors are described in detail in ten Dijke et al. (1993) *Oncogene* 8:2879–2887; and (1994) *Science* 264:101–104. The general structures of these proteins is described in FIG. 1, and the sequence alignments between the ALK genes are shown in FIGS. 2 and 3. These molecules have similar domain structures: an N-terminal predicted hydrophobic signal sequence (von Heijne (1986) Nucl. Acids Res. 14: 4683–4690) is followed by a relatively small extracellular cysteine-rich ligand binding domain, a single hydrophobic transmembrane region (Kyte & Doolittle (1982) J. Mol. Biol. 157, 105–132) and a C-terminal intracellular portion, which consists almost entirely of a kinase domain (FIG. 3).

The extracellular domains of these receptors, defined essentially by residues 22–118 (SEQ. ID NO:2) for ALK-1; residues 16–123 (SEQ ID NO:4) for ALK-2; residues 24–152 (SEQ. ID NO:6) for ALK-3; and residues 23–122 (SEQ ID NO:8) for ALK-6, have cysteine-rich regions, but sequence similarity varies among the proteins. For example, ALK-3 and ALK-6 share a high degree of sequence similarity in their extracellular domains (46% identity) whereas ALK-2 shows less similarity with ALK-3 or ALK6 (see FIG. 2.)

The positions of many of the cysteine residues in these receptors can be aligned, indicating that the extracellular domains likely adopt a similar structural configuration.

The intracellular domains of these receptors are characterized by a serine/threonine kinase, defined essentially by residues 204–494 (SEQ. ID. No. 1) for ALK-1; residues 210–510 (SEQ ID No. 3) for ALK-2; residues 236–527 (SEQ ID No. 5) for ALK-3; and residues 206–497 (SEQ ID No. 7) for ALK-6. The catalytic domains of kinases can be divided into 12 subdomains with stretches of conserved amino-acid residues. The key motifs are found in serine/threonine kinase receptors indicating that they are functional kinases. The consensus sequence for the binding of ATP (Gly-X-Gly-X-X-Gly (SEQ ID NO:16) in subdomain I followed by a Lys residue further downstream in subdomain II) is found in all the ALKS. Moreover, ALK-1, ALK-2, ALK-3 and ALK-6 have the sequence motifs or similar motifs HRDLKSKN (Subdomain VIB (SEQ ID NO:17)) and GTKRYMAPE (Subdomain VIII (SEQ ID NO:18)), that are found in most of the serine/threonine kinase receptors and can be used to distinguish them from tyrosine kinase receptors. Two short inserts in the kinase domain (between subdomain VIA and VIB and between X and XI are unique to members of this serine/threonine kinase receptor family. In the intracellular domain, these regions, together with the juxtamembrane part and C-terminal tail, are the most divergent between family members.

Type II serine/threonine kinase receptors known in the art are described and referenced herein above.

EXAMPLE 2

RECEPTOR EXPRESSION

A. General Considerations

Receptor DNA, or a synthetic form thereof, can be inserted, using conventional techniques well described in the art (see, for example, Maniatis (1989) *Molecular Cloning A Laboratory Manual*), into any of a variety of expression vectors and transfected into an appropriate host cell to produce recombinant protein polypeptide chains, including both full length and truncated forms thereof. Shortened sequences, for example, can be used for the production of soluble receptor fragments.

Useful host cells include *E. coli, Saccharomyces cerevisiae, Pichia pastoris*, the insect/baculovirus cell system, myeloma cells, and various other mammalian cells. The full length forms of the proteins of this invention preferably are expressed in mammalian cells, as disclosed herein. Soluble forms may be expressed from both mammalian or bacterial cell systems. The vector additionally may include various sequences to promote correct expression of the recombinant protein, including transcription promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant morphogen receptor also may be expressed as a fusion protein. After translation, the protein may be purified from the cells themselves or recovered from the culture medium. The DNA also may include sequences which aid in expression and/or purification of the recombinant protein. One useful sequence for example, is a hexa-His (His$_6$) sequence, which adds a histidine tail to allow affinity purification of the protein on an IMAC Cu2+ column (see below.)

For example, the DNA encoding the extracellular domain may be inserted into a suitable expression vector for transformation into a prokaryote host such as *E. coli* or *B. subtilis*, to produce a soluble, morphogen binding fragment. The DNA may expressed directly or may be expressed as part of a fusion protein having a readily cleavable fusion junction. An exemplary protocol for prokaryote expression using MR-1 DNA is provided below. Recombinant protein is expressed in inclusion bodies and may be purified therefrom using the technology disclosed in U.S. Pat. No. 5,013,653, for example.

The DNA also may be expressed in a suitable mammalian host. Useful hosts include fibroblast 3T3 cells, (e.g., NIH 3T3, from CRL 1658) COS (simian kidney ATCC, CRL- 1650) or CHO (Chinese hamster ovary) cells (e.g., CHO-DXB11, from Lawrence Chasin, *Proc. Nat'l. Acad. Sci.* (1980) 77(7):4216–4222), mink-lung epithelial cells (MV1Lu), human foreskin fibroblast cells, human glioblastoma cells, and teratocarcinoma cells. Other useful eukaryotic cell systems include yeast cells, the insect/baculovirus system or myeloma cells.

To express an OP1-specific cell surface receptor, the DNA is subcloned into an insertion site of a suitable, commercially available vector along with suitable promoter/enhancer sequences and 3' termination sequences. Useful promoter/enhancer sequence combinations include the CMV promoter (human cytomegalovirus (MIE) promoter) present, for example, on pCDM8, as well as the mammary tumor virus promoter (MMTV) boosted by the Rous sarcoma virus LTR enhancer sequence (e.g., from Clontech, Inc., Palo Alto). A useful induceable promoter includes, for example, A $Zn^{2+}$induceable promoter, such as the $Zn^{2+}$ metallothionein promoter (Wrana et al. (1992) *Cell* 71:1003–1014.) Other induceable promoters are well known in the art and can be used with similar success. Expression also may be further enhanced using transactivating enhancer sequences. The plasmid also preferably contains an amplifiable marker, such as DHFR under suitable promoter control, e.g., SV40 early promoter (ATCC #37148). Transfection, cell culturing, gene amplification and protein expression conditions are standard conditions, well known in the art, such as are described, for example in Ausubel et al., ed., *Current Protocols in Molecular Biology*, John Wiley & Sons, NY (1989). Briefly, transfected cells are cultured in medium containing 5–10% dialyzed fetal calf serum (FCS), and stably transfected high expression cell lines obtained by amplification and subcloning and evaluated by standard Western and Northern blot analysis. Southern blots also can be used to assess the state of integrated receptor sequences and the extent of their copy number amplification.

The expressed protein then is purified using standard procedures. A currently preferred methodology uses an affinity column, such as a ligand affinity column or an antibody affinity column, the bound material then washed, and receptor molecules selectively eluted in a gradient of increasing ionic strength, changes in pH or addition of mild denaturants. Alternatively, where a useful anchor sequence has been added to the DNA, such as a $(His)_6$ sequence, the column may be a standard affinity column such as $Cu^{2+}$ IMAC column. Here, for example, the cell culture media containing the recombinant protein is passed over a $Cu^{2+}$ IMAC column (for example, prepared with 25 mM imidazole). The bound protein then is washed with a compatible solution and eluted with EDTA. The anchor sequence can be removed by a standard chemical or enzymatic procedure.

Mammalian cell expression is preferred where morphogen receptor expression on a cell surface is desired For example, cell surface expression may be desired to test morphogen or morphogen analog binding specificity for a cell surface receptor under in vivo conditions. Cell surface expression also may be most efficacious for medium flux cellular screen assays as described below.

B.1 Exemplary Mammalian Cell Culture

The receptors tested in Examples 8 and 9 described below were expressed in (1) COS-1 cells; (2) mink lung epithelial cells (Mv1Lu); (3) AG1518 human foreskin fibroblasts; (4) MG-63 human osteosarcoma cells; (5) PC12 rat pheochromocytoma cells (all obtained from American Type Culture Collection, Rockville, Md.); (6) U-1240 MG human glioblastoma cells (Bengt Westermark, et al. (1988) *Cancer Research* 48:3910–3918); (7) Tera-2 teratocarcinoma cells (clone 13, Thompson et al. (1984) J Cell Sci 72:37–64); (8) MC3T3-El cells (Sudo et al. (1983) *J. Cell Biol.* 96:191–198, and (9) ROS 17/2.8 rat osteosarcoma cells (Majeska et al. (1985) *Endocrinology* 116:170–179. The ROS cells were cultured in Ham's F12 medium containing 14 mM HEPES buffer, 2.5 mM L-glutamine, 1.1 mM $CaCl_2$, 5% fetal bovine serum and antibiotics; MC3T3-E1 cells were cultured in a-MEM with 10% fetal bovine serum and antibiotics, and Tera-2 cells were cultured in 5% $CO_2$ atmosphere at 37° C. in a-MEM containing 10% fetal bovine serum, 100 units/ml of penicillin and 50 mg/ml of streptomycin, using tissue culture dishes pretreated with 0.1% swine skin gelatin (Sigma) in phosphate-buffered saline. Unless otherwise specified, cells were cultured in DMEM containing 10% fetal bovine serum and antibiotics.

B.2 Transfection of cDNA

The receptors tested in EXAMPLE 8.1 (ALK 1–6, daf-4) were transfected as follows. Transient expression plasmids of ALK-1 to -6 and daf-4 were generated by subcloning into an expression vector (pSV7d, Truett et al. (1985) DNA 4:333–349) or into the pcDNA I expression vector (Invitrogen, San Diego). For transient transfection, COS-1 cells were transfected with 10 mg each of plasmids by a calcium phosphate precipitation method using a mammalian transfection kit (Stratagene, La Jolla), following the manufacturer's protocol. One day after transfection, the cells were used for the affinity labeling and cross-linking experiments.

EXAMPLE 3

ANTIBODY PRODUCTION

A. General Considerations

Antibodies capable of specifically binding the receptor molecules, ligand molecules, or the ligand-receptor complex itself, useful as analogs and useful in immunoassays and in the immunopurification of morphogen receptors described may be obtained as described below.

Where antibodies specific to the OP-1 specific receptors are desired, but which do not interfere with ligand binding, the antigenic sequence preferably comprises the juxtamembrane sequence. Where antibodies capable of competing for ligand binding are desired, the ligand binding domain may be used as the antigen source. Where antibodies to the complex are desired, the complex itself preferably is used as the antigenic sequence and candidate antibodies then tested for cross reactivity with uncomplexed ligand and receptors versus the ligand-receptor complex. Finally, bispecific antibodies may used to complex ligand to a cell surface receptor (Type I or Type II) and/or to target an agent or ligand to cells or tissue expressing a Type I or Type II morphogen-specific receptor. Preferred bispecific antibody derived molecules are single chain binding sites described in U.S. Pat. No. 5,091,513 and 5,132,405, the disclosures of which are incorporated hereinabove by reference.

Antibodies useful as OP-1 receptor-binding analogs may be obtained using the receptor ligand binding domain as the immunogen source and testing receptor-binding analogs for their ability to compete with OP-1 in a competition binding assay. Similarly, where antibodies useful as OP-1 specific receptor analogs are desired, OP-1 is the immunogen source and the antibody candidate tested in a competition assay with receptor protein.

Polyclonal antibodies specific for a morphogen receptor of interest may be prepared generally as described below. Each rabbit is given a primary immunization (e.g., 500 mg) of antigen in 0.1% SDS mixed with 500 ml Complete Freund's Adjuvant. The antigen is injected intradermally at multiple sites on the back and flanks of the animal. The rabbit is boosted after a month with 500 mg of antigen in the same manner using incomplete Freund's Adjuvant. Test bleeds are taken from the ear vein seven days later. Two additional boosts and test bleeds are performed at monthly intervals until antibody against the antigenic sequence is detected in the serum using a standard Western blot. Then, the rabbit is boosted monthly with 100 mg/ml of antigen and bled (15 ml per bleed) at days seven and ten after boosting.

Similarly, monoclonal antibodies specific for a given morphogen receptor molecule of interest may be prepared as described below: A mouse is given two injections of the antigenic sequence. The protein preferably is recombinantly produced. Where it is desired that the antibody recognize an epitope on the morphogen binding surface of a receptor an antigenic fragment derived from the extracellular domain preferably is provided. The first injection contains 100 mg of antigen in complete Freund's adjuvant and is given subcutaneously. The second injection contains 50 mg of antigen in incomplete adjuvant and is given intraperitoneally. The mouse then receives a total of 230 mg of antigen in four intraperitoneal injections at various times over an eight month period. One week prior to fusion, the mouse is boosted intraperitoneally with antigen (e.g., 100 mg) and may be additionally boosted with an antigen-specific peptide conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for ALK-specific antibodies, e.g., using ALK-2, ALK-3 or ALK-6 as antigen. The cell fusion and monoclonal screening steps readily are performed according to standard procedures well described in standard texts widely available in the art. (See, for example, *Guide to Protein Purification* Murray P. Deutscher, ed., Academic Press, San Diego, 1990.

B. Exemplary ALK-Specific Antisera

Antibodies used in the assay of EXAMPLE 8 were obtained as follows. Rabbit antisera against ALK-1 to -6 were made against synthetic peptides corresponding to the divergent, intracellular juxtamembrane parts. (ALK-1: residues 119–141; ALK-2: residues 151–172; ALK-3 residues 181–202; ALK-6: residues 151–168.) Peptides were synthesized with an Applied Biosystems 430 A Peptide Synthesizer using t-butoxycarbonyl chemistry, and purified by reverse phase HPLC. The synthetic peptides were coupled to keyhole limpet hemocyanin (Calbiochem-Behring) using glutaraldehyde, as decribed by Gullick et al. (1985) *EMBO J* 4: 2869–2877. The coupled peptides then were mixed with Freund's adjuvant and used to immunize rabbits using standard methodologies.

EXAMPLE 4

OP1-RECEPTOR BINDING ASSAYS

Ligand binding specificity is determined by evaluating the ability of a receptor molecule to bind a specific ligand, and the ability of that ligand to compete against itself and other molecules which bind the receptor. Useful ligands will have a binding affinity for a soluble morphogen receptor extracellular domain such that dissociation constant (Kd) is less than about $10^{-6}$M, preferably less than $5\times10^{-7}$M. Where stronger binding interaction is desired, preferred affinities are defined by a Kd of $10^{-8}$–$10^{-9}$M. OP1-related proteins are expected to be able to bind with specificity to multiple different receptor molecules, although likely with differing affinities.

Ligand binding specificity can be assayed as follows, essentially following standard protocols well described in the art and disclosed, for example, in Legerski et al. (1992) *Biochem. Biophys. Res. Comm* 183:672–679 and Frakar et al., (1978) *Biochem. Biophys. Res.Comm.* 80:849–857. In the ligand binding assays, a ligand having a known, quantifiable affinity for a morphogen receptor molecule of interest is labelled, typically by radioiodination ($^{125}$I), e.g., by chromogenic or fluorogenic labeling, or by metabolic labelling, e.g., $^{35}$S, and aliquots of cells expressing the receptor on their surface are incubated with the labelled ligand, in the presence of various concentrations of unlabelled potential competitor ligand. In the assays described in Examples 8 and 9, below, this competitor typically is the candidate morphogen analog or an aliquot from a broth or extract anticipated to contain a candidate morphogen analog.

Alternatively, a crosslinking agent may be used to covalently link the ligand to the bound receptor, and the crosslinked complex then immunoprecipitated with an antibody specific to the ligand, receptor, or complex. (See, Example 8.)

A standard, exemplary protocol for determining binding affinity is provided below. Briefly, cells expressing a receptor on their cell surface are plated into 35 mM dishes and incubated for 48 hours in DMEM (Dulbeccol's modified Eagle medium) plus 10% fetal calf serum. Purified morphogen, here, e.g., OP-1, or an OP1-analog is iodinated with Na$^{125}$I by chloramine T oxidation, preferably having a specific activity of about 50–100 mCi/mg, essentially following the protocol of Frolik et al. (1984) *J. Biol. Chem.* 595:10995–11000. Labelled morphogen then is purified using standard procedures, e.g., chromatographically. Plated cells then are washed twice with physiologically buffered saline in the presence of 0.1% BSA, and incubated at 22° C. in the presence of BSA, buffer and labelled morphogen (1 ng) and various concentrations (e.g., 0–10 mg/ml) of unlabelled competitor, e.g., unlabelled morphogen or candidate ligand analogs. Following binding, cells are washed three times with cold buffer, solubilized in 0.5 ml of 0.5 N NaOH, removed from the dish, and radioactivity determined by gamma or scintillation counter. Data then are expressed as percent inhibition, where 100% inhibition of specific binding is the difference between binding in the absence of competitor and binding in the presence of a 100-fold molar excess of unlabelled morphogen. Binding parameters preferably are determined using a computer program such as LIGAND (Munsun et al. (1980) *Anal. Biochem.* 107:220–259.)

Where the receptor cell surface binding domain is to be provided as a soluble protein, the assay can be performed in solution, most readily as an immunoprecipitation assay. In currently preferred assays the morphogen molecule is labelled and incubated with unlabelled receptor and candidate morphogen analogs. Receptor-specific antibody then is provided to the solution to precipitate the receptor-morphogen complex and the amount of labelled morphogen in the precipitated complex determined using standard detection means.

Where the receptor or ligand is to be used in an affinity isolation protocol, the molecule preferably is immobilized on a surface, preferably a matrix surface over which sample fluid will flow, allowing the ligand of interest to bind, at letting nonbinding components pass through as effluent. The complex then can be removed intact or the ligand selectively removed with a desired eluant.

4.1 SCREENING ASSAY CONSIDERATIONS

In the analog screening assays described in Example 9 below, the preferred protocol for assaying ligand-receptor binding is a standard competition or radioimmunoassay (RIA). Here the OP-1 is labelled and the relative binding affinity of a candidate OP-1 analog ligand in a sample is measured by quantitating the ability of the candidate (unlabelled ligand analog) to inhibit binding of the labelled ligand (competitor morphogen) by the receptor. In performing the assay, fixed concentrations of receptor and labelled morphogen are incubated in the absence and presence of unknown samples containing candidate ligands. Sensitivity can be increased by preincubating the receptor with candidate ligand before adding the labelled morphogen. After the labelled competitor has been added, sufficient time is allowed for adequate competitor binding, and then free and bound labelled morphogen are separated, and one or the other is measured. Useful morphogen labels include radioactive labels, chromogenic or fluorogenic labels, and conjugated enzymes having high turnover numbers, such as horseradish peroxidase, alkaline phosphatase, or β-galactosidase, used in combination with chemiluminescent or fluorogenic substrates In the same manner, OP-1 specific receptor analogs can be assayed for their affinity for OP-1 in competition assays with labelled OP1 specific receptors.

Assays for evaluating a candidate OP-1 receptor-binding analog's ability to mimic OP-1 in signal-transduction across a membrane are exemplified in detail in EXAMPLE 9.2, below. Briefly, the assay involves use of a cell (1) known to express an OP-1-specific receptor; or (2) which can be modified to express an OP-1-specific receptor, and/or (3) which can induce an OP-1-mediated cellular response. In the assay, the ability of a candidate analog to induce an OP-1-specific cellular response is monitored. Numerous OP-1-responsive cells and OP-1-mediated inducible cellular and biochemical markers are known and described in the art. Alternatively, and as exemplified below, an OP-1 inducible reporter gene system can be constructed and used to advantage in the assay.

4.2 DIAGNOSTIC ASSAY CONSIDERATIONS

The ability to detect morphogens in solution provides a valuable tool for diagnostic assays, allowing one to monitor the level of morphogen free in the body, e.g., in serum and other body fluids. For example, OP-1 has been detected in a number of different body fluids, including serum and spinal fluid, including cerebro-spinal fluid, saliva, milk and other breast exudates. (See, for example, PCT US92/07432, PCT US93/07231, WO94/06449).

As one example, OP-1 is an intimate participant in normal bone growth and resorption. Thus, soluble OP-1 is expected to be detected at higher concentrations in individuals experiencing high bone formation, such as children, and at substantially lower levels in individuals with abnormally low rates of bone formation, such as patients with osteoporosis, a plastic bone disease, or osteopenia. Monitoring the level of OP-1 in serum thus provides a means for evaluating the status of bone tissue and bone homeostasis in an individual, as well as a means for monitoring the efficacy of a treatment to regenerate damaged or lost bone tissue. Alternatively, the level of OP-1 in bone tissue can be assessed in a bone tissue biopsy.

Similarly, OP-1 and other morphogens have been identified in brain tissue. In particular, OP-1 is expressed and/or localized in developing and adult rat brain and spinal cord tissue, in the hippocampus, substantia nigra and the adendema glial cells, as well as associated with astrocytes and the extracellular matrix surrounding neuronal cell bodies. (See, PCTUS93/07331). Thus, monitoring the level of OP-1 in spinal fluid or associated with a nerve tissue biopsy can provide means for evaluating the status of nerve tissue in an individual, as well as means for monitoring the efficacy of a nerve regeration or repair therapy.

For serum assays, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble morphogen complex or mature morphogens relative to that of the other proteins present in serum. Further purification also can be achieved by chromatographic techniques well known in the art. The sample fluid then can be assayed for OP-1 using the OP1-specific receptor(s) and binding assays as described herein.

For a tissue biopsy, cells can be collected and stained with a labelled OP-1-specific antibody or receptor molecule. Alternatively, the OP-1 protein selectively can be extracted and quantitated as described above.

Morphogens useful in the binding/screening assays contemplated herein include the soluble forms of the protein, e.g., the mature dimeric species complexed with one or two copies of the pro domain, the mature dimeric species alone, and truncated forms comprising essentially just the C-terminal active domain.

EXAMPLE 5

TRANSMEMBRANE SIGNAL INDUCTION ASSAYS/OP1 MIMETICS

The kinase activity of the intracellular domains of the OP1-specific receptors can be tested in an autophophorylation assay as described by Mathews et al. (PCT/US92/03825, published Nov. 26, 1992). Briefly, the DNA fragment encoding at least the intracellular kinase domain of an OP1-specific receptor is subcloned into pGEX-2T (Smith et al.(1988) Gene 67:31–40) to create a fusion protein between the putative kinase domain and glutathione S-transferase (GST). The plasmid is introduced into *E. coli* and the expressed fusion protein purified using glutathione affinity chromatography. About 100–200 ng of fusion protein or purified GST then are incubated with 25 mCi (gp$^{32}$P) ATP in 50 mM tris, 10 mM MgCl$_2$ buffer for 30 minutes at 37° C. Products then are analyzed by gel electrophoresis and autoradiography. The fusion protein, but not GST alone, becomes phophorylated, indicating that the kinase domain is functional. Phosphoamino acid analysis then can be performed to determine the predominant amino acid being phosphorylated. Similar assays can be performed using similar fusion constructs expressed in mammalian cells.

Various signaling transduction assays are provided in Example 9, below. An assay also can be developed for testing kinase activity transduction upon ligand binding using a ligand-induced kinase activity assay known in the art. Here, the ability of OP-1 analog to induce phosphorylation upon binding to the receptor is tested.

See, for example, various assays for measuring ligand-induced kinase activity described by Accili et al. (1991) *J. Biol.Chem.* 266:434–439 and Nakamura et al. (1992) *J.Biol. Chem.* 267: 18924–18928,. For example, ligand-induced kinase activity (e.g., receptor autophosphorylation) can be measured in vitro by incubating purified receptor in the presence and absence of ligand (here, OP1 or OP1 analog, e.g., $10^{-7}$M) under conditions sufficient to allow binding of the ligand to the receptor, followed by exposure to $^{32}$P-ATP (e.g., 100 mCi in the presence of 10 mM Tris-HCl (pH 7.6), 10 mM MgCl$_2$, 10 mM MnCl$_2$, 1 mM dithiothreitol, 0.15M NaCl$_2$, 0.1% Triton X-100 and 3% glycerol) and the amount of phosphorylation measured, e.g., by SDS polyacrylamide gel electrophoresis and autoradiography following immmunoprecipitation with antiphosphoserine, antiphosphothreonine or antiphosphotyrosine antibody (e.g., commercially available or made using standard antibody methodologies.) While a low level of autophosphorylation may be detected in the absence of ligand, incubation with ligand is anticipated to significantly increase (e.g., 5–20 fold increase) the amount of phosphorylation detected.

In another assay for detecting ligand-induced receptor autophosphorylation, involving intact cells, receptor DNA is transfected into a suitable host cell, e.g., a fibroblast, which then is grown under standard conditions to create a confluent monolayer of cells expressing the receptor on their cell surface. On the day of the experiment, cells are incubated with or without ligand (e.g., OP-1 or OP-L analog, e.g., $10^{-7}$M) at 37° C., and then quickly washed with a "stopping solution" containing ATP (e.g., 0.1 M NaF, 4 mM EDTA, 10 mM ATP, 10 mM sodium orthovanadate, 4 mM sodium pyrophosphate). The cells then are frozen in a dry ice/ethanol bath, solubilized and the receptors immunoprecipitated, e.g., with an antireceptor antibody, as described herein. The immune complexes then are segregated, washed, separated by gel electrophoresis using standard procedures and transferred to a membrane for Western blot analysis using standard procedures. Phosphorylation of the receptor then can be visualized by immunodetection with a suitable antibody (e.g., antiphosphoserine, antiphosphothreonine or antiphosphotyrosine), as described above. The bound antibody (e.g., bound antiphosphoserine, antiphosphothreonine or antiphosphotyrosine) then can be detected with $^{125}$I labelled protein A, followed by autoradiography. The amount of phosphorylated receptor detected is anticipated to be significantly greater (5–20 fold increase) in receptors incubated with ligand than receptors exposed to ATP in the absence of ligand.

Ligand-induced receptor phosphorylation of exogenous substrates similarly can be assayed essentially using the methodology described herein. Here, a suitable substrate (e.g., a synthetic polypeptide containing serine, threonine or tyrosine amino acids) is provided to the receptor following ligand exposure and prior to incubation with ATP. The substrate subsequently can be segregated by immunoprecipitation with an antibody specific for the substrate, and phosphorylation detected as described above. As for autophosphorylation, the amount of phosphorylated substrate detected following ligand incubation is anticipated to be greater than that detected for substrates exposed to receptors in the absence of ligand.

Alternatively, a reporter gene construct can be created to assay transmembrane signal induction. Here, the expression control elements for an OP-1 inducible protein marker is fused to the open reading frame sequence for any reporter gene, and induction of the reporter gene expression then assayed. Useful reporter genes include the luciferase gene or GAL4 as well as other, easily characterizable markers.

EXAMPLE 6

CHIMERIC RECEPTOR MOLECULES

Chimeric receptor molecules, e.g., comprising an ALK or ALK analog extracellular and transmembrane region and, for example, part or all of an intracellular domain from another, different receptor or an intracellular domain from a different cell surface molecule, may be constructed using standard recombinant DNA technology and/or an automated DNA synthesizer to construct the desired sequence. As will be appreciated by persons skilled in the art, useful junctions include sequences within the transmembrane region and/or sequences at the junction of either the intracellular or the extracellular domains. Also envisioned are chimers where the extracellular domain or the intracellular domains themselves are chimeric sequences.

Chimeric sequences are envisioned to be particularly useful in screening assays to determine candidate binding ligands (e.g., OP-1 analogs, see below), where the non-receptor intracellular domain provides a suitable second messenger response system that is easy to detect. Potentially useful other second messenger response systems include those which, when activated, induce phosphoinositide hydrolysis, adenylate cyclase, guanylate cyclase or ion channels.

Chimeric receptor molecules have particular utility in gene therapy protocols. For example, a population of cells expressing a chimeric morphogen receptor molecule on their surface and competent for expressing a desired phenotype can be implanted in a mammal at a particular tissue locus. By careful choice of the ligand binding domain used on these receptors a physician can administer to the individual a morphogen agonist capable of: (1) binding to the chimeric receptor alone and (2) stimulating the proliferation and/or differentiation of the implanted cells without affecting endogenous cell populations.

EXAMPLE 7

CONSIDERATIONS FOR IDENTIFYING OTHER OP1 SPECIFIC RECEPTORS IN NUCLEIC ACID LIBRARIES

Identification of ALK Type I receptors that can bind OP-1 allows one to identify other morphogen receptor sequences in different species as well as in different tissues. The OP1-binding ALK sequences themselves can be used as a probe or the sequence may be modified to account for other potential codon usage (e.g., human codon bias.) Currently preferred probe sequences are those which encode the receptor's extracellular domain.

Probes based on the nucleic acid sequence of SOQ. ID Nos.1, 3, 5or 7 can be synthesized on commercially available DNA synthesizers, e.g. Applied Biosystems model 381A, using standard techniques, e.g. Gait, *Oligonucleotide Synthesis: A Practical Approach*, (IRL Press, Washington D.C., 1984). It is preferable that the probes are at least 8–50 bases long, more preferably 18–30 bases long. Probes can be labeled in a variety of ways standard in the art, e.g. using radioactive, enzymatic or colorimetric labels as described, for example, by Berent et al, (May/June 1985) *Biotechniques*: 208–220; and Jablonski et al, (1986) *Nucleic Acids Research* 14: 6115–6128.

Preferably, low stringency conditions are employed when screening a library for morphogen receptor sequences using a probe derived from OP1-binding receptor. Preferred ALK-specific probes are those corresponding to bases encoding the extracellular domain ("ECD"), or encoding a unique (nonhomologous) sequence within the cytoplasmic domain. Useful probes may be designed from bases encoding the juxtamembrane region, for example. The probe may be further modified to use a preferred species codon bias.

Alternatively, probes derived from the serine/threonine kinase domain can be used to identify new members of the receptor kinase family which can be screened for OP1 binding using the methods described in Example 8.

For example, for a probe of about 20–40 bases a typical prehybridization, hybridization, and wash protocol is as follows:

(1) prehybridization: incubate nitrocellulose filters containing the denatured target DNA for 3–4 hours at 55° C. in 5×Denhardt's solution, 6×SSC (20×SSC consists of 175g NaCl, 88.2 g sodium citrate in 800 ml $H_2O$ adjusted to pH. 7.0 with 10N NaOH), 0.1% SDS, and 100 mg/ml denatured salmon sperm DNA, (2) hybridization: incubate filters in prehybridization solution plus probe at 42° C. for 14–48 hours, (3) wash; three 15 minutes washes in 6×SSC and 0.1% SDS at room temperature, followed by a final 1–1.5 minute wash in 6×SSC and 0.1% SDS at 55° C. Other equivalent procedures, e.g. employing organic solvents such as formamide, are well known in the art.

Alternatively, morphogen receptor-specific DNA can be amplified using a standard PCR (polymerase chain reaction) methodology such as the one disclosed herein, to amplify approximately 500 base pair fragments. As for the hybridization screening probes described above, the primer sequences preferably are derived from conserved sequences in the serine/threonine kinase domain. The primers disclosed herein, in Seq. ID Nos. 12–15 are envisioned to be particularly useful, particularly in combination.

Examples of useful PCR amplifications, including the use of the primers recited herein, are disclosed in ten Dijke, et al. (1993) *Oncogene* 8:2879–2887 and (1994) *Science* 264:101–104, and which also describe the isolation protocols for ALK-1, ALK-2, ALK-3 and ALK-6.

7.1 TISSUE DISTRIBUTION OF MORPHOGEN RECEPTORS

Determining the tissue distribution of OP-1-specific receptors can be used to identify tissue and cell sources which express these receptors, to identify new, related OP-1-specific receptor molecules, as well as to identify target tissues for OP-1-receptor interactions under naturally occurring conditions. The OP-1 specific receptor molecules (or their mRNA transcripts) readily are identified in different tissues using standard methodologies and minor modifications thereof in tissues where expression may be low. For example, protein distribution can be determined using standard Western blot analysis or immunohistological detection techniques, and antibodies specific to the morphogen receptor molecules of interest. Similarly, the distribution of morphogen receptor transcripts can be determined using standard Northern hybridization protocols and transcript-specific probes or by in situ hybridization.

Any probe capable of hybridizing specifically to a transcript, and distinguishing the transcript of interest from other related transcripts can be used. Because the morphogen receptors described herein likely share high sequence homology in their intracellular domains, the tissue distribution of a specific morphogen receptor transcript may best be determined using a probe specific for the extracellular domain of the molecule. For example, a particularly useful ALK-specific probe sequence is one derived from a unique portion of the 5' coding sequence, the sequence corresponding to the juxtamembrane region, or the 5' or 3' noncoding sequences. The chosen fragment then is labelled using standard means well known and described in the art and herein.

Using these receptor-specific probes, which can be synthetically engineered or obtained from cloned sequences, receptor transcripts can be identified and localized in various tissues of various organisms, using standard methodologies well known to those having ordinary skill in the art. A detailed description of a suitable hybridization protocol is described in Ozkaynak, et al., (1991) *Biochem. Biophys. Res. Commn.* 179:116–123, and Ozkaynak, et al. (1992) *J Biol. Chem.* 267:25220–25227. Briefly, total RNA is prepared from various tissues (e.g., murine embryo and developing and adult liver, kidney, testis, heart, brain, thymus, stomach) by a standard methodologies such as by the method of Chomczynski et al. ((1987) *Anal. Biochem* 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 mg) from each tissue is fractionated on a 1% agarose/formaldehyde gel and transferred onto a Nytran membrane (Schleicher & Schuell). Following the transfer, the membrane is baked at 8° C. and the RNA is cross-linked under UV light (generally 30 seconds at 1 $mW/cm^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5×Denhardts, 5×SSPE, and 0.1% SDS. Following hybridization, the non-specific counts are washed off the filters in 0.1×SSPE, 0.1% SDS at 5° C.

EXAMPLE 8

DEMONSTRATION THAT ALK-2, ALK-3 AND ALK-6 ARE OP1-BINDING RECEPTORS

The tissue morphogenic proteins OP-1 and BMP-4 were tested for specific binding interaction with the ALK receptors in receptor-transfected cells (where the receptor is over-expressed), and in nontransfected cells. It previously was known that ALK-5 interacted specifically with TGF91 and ALK-2 and ALK-4 interacted specifically with activin. In the experiment, complexes were crosslinked and immuno-precipitated with an ALK-specific antibody as described below. To date, no binding with ALK-1 under the conditions of this protocol have been detected.

Binding and affinity cross-linking using disuccinimidyl suberate (Pierce Chemical Co.) were performed using standard methods (e.g., Franzen et al. (1993) *Cell* 75:681–692 and Ichijo et al. (1990) *Exp. Cell Res.* 187:10995–11000.) A typical protocol is described below. Modifications from this protocol for individual experiments were standard changes anticipated to produce the same result as for the recited procedure. Briefly, cells in multi-well plates were washed with binding buffer (e.g., phosphate buffered saline containing 0.9 mM $CaCl_2$, 0.49 mM $MgCl_2$ and 1 mg/ml bovine serum albumin (BSA)), incubated on ice in the same buffer with labelled ligand, in the presence and absence of excess unlabelled ligand for sufficient time for the reaction to equilibrate (e.g., 3 hours.) Cells were washed and the crosslinking was done in the binding buffer without BSA together with 0.28 mM disuccinimidyl suberate for 15 min on ice. Cells were harvested by addition of 1 ml of detachment buffer (10 mM Tris-HCl, pH 7.4, 1 mM EDTA, 10% glycerol, 0.3 mM PMSF.) Cells then were pelleted by centrifugation, then resuspended in 50 ml of solubilization buffer (125 mM NaCl, 10 mM Tris-HCl, pH 7.4, 1 mM EDTA, 1% Triton X-100, 0.3 mM PMSF, 1% Trasylol) and incubated for 40 minutes on ice. Cells were centrifuged again and supernatants subjected to analysis by standard SDS-gel electrophoresis using 4%–15% polyacrylamide gels, followed by autoradiography.

Cell lysates obtained following affinity cross-linking via the general protocol described above were immunoprecipitated using antisera against ALKs (e.g., raised against the ALK juxtamembrane region), or directly analyzed by SDS-gel electrophoresis using gradient gels consisting of 5–12% or 5–10% polyacrylamide. The gels were fixed and dried, and then subjected to autoradiography or analysis using phosphornmager (Molecular Dynamics).

8.1 BINDING OF OP-1 AND/OR BMP-4 TO ALKS IN TRANSFECTED CELLS

COS-1 cells transfected with ALK cDNA were tested for the binding of $^{125}$I-OP-1 and $^{125}$I-BMP-4, in the presence or absence of co-transfected Type II receptor DNA: daf-4 cDNA or ActRII (Estevez et al. (1993) *Nature* 365:644–649 and Attisano et al. (1992) *Cell* 68:97–108, disclosing the DNA sequence for these Type II receptors and the disclosure of which is incorporated herein by reference.) Since the cross-linked complexes were sometimes difficult to visualize because of high background, samples were immunoprecipitated by antisera against each ALK. The results are presented in Table I below. In the Table, "NIT" means "not tested". Binding was specific as determined by standard competition assays. The values represented by "+/−", "+", "++", "+++", and "−" are all qualitative descriptors of the relative amount of radioactivity measured when the crosslinked molecules were gel electrophoresed and subjected to autoradiography. More radioactivity measured indicates a stronger binding interaction detected. In the Table the strength of binding interaction is as follows: +++>++>+>+/−>−.

TABLE I

| | $^{125}$I OPI | | | | $^{125}$I BMP4 | | |
|---|---|---|---|---|---|---|---|
| | +daf4 | −daf4 | ActRII | | +daf4 | −daf4 | +ActRII |
| ALK1 | − | − | − | ALK1 | − | − | N/T |
| ALK2 | ++ | +/− | ++ | ALK2 | − | − | N/T |
| ALK3 | ++ | − | +/− | ALK3 | +++ | ++ | N/T |
| ALK4 | − | − | − | ALK4 | − | − | N/T |
| ALK5 | − | − | − | ALK5 | − | − | N/T |
| ALK6 | +++ | ++ | + | ALK6 | +++ | +++ | N/T |

In the absence of daf-4, OP-1 bound to ALK-6, whereas BMP-4 bound to ALK-3 and ALK-6. Weaker binding of OP-1 to ALK-2 was also observed. Other ALKs did not bind OP-1 or BMP-4 in the absence of Daf-4. When ALK cDNAs were co-transfected with the daf-4 cDNA, increased binding of OP-1 to ALK-2 and ALK-6 was seen. In addition, ALK-3 also was found to bind OP-1 in the co-transfected cells. Similarly, increased binding of BMP-4 to ALK-3 and ALK-6 could be observed. Co-transfection of two different types of ALKs did not further increase the binding of OP-1 or BMP-4. In cells co-transfected with the DNA for ActRII and ALK-2, ALK-3 or ALK-6, OP-1-receptor binding was enhanced.

The sizes of the cross-linked complexes were slightly higher for ALK-3 than for ALK-2 and ALK-6, consistent with its slightly larger size. Complexes of about 95 kDa as well as multiple components of 140–250 kDa were also co-immunoprecipitated with certain of the ALKs.

In standard competition assays performed with the Type I receptors in the presence and absence of the Type II receptors, the binding of OP-1 and BMP-4 could be competed with excess amounts of unlabeled OP-1, verifying the binding specificity of these interactions where they occurred.

These results demonstrate that ALK-2, ALK-3 and ALK-6 can serve as Type I receptors for OP-1. Notably, ligand binding apparently can be enhanced in the presence of Type II receptors. Moreover, OP-1 is able to interact with both a "bone morphogen" Type II receptor (daf 4) and an "activin" Type II receptor (ActRII), whereas, for example, activin only interacts with the ActRII Type II receptor. The data indicate that OP-1 has a broader spectrum of receptor (Type I and Type II) binding affinities than do other tissue morphogenic proteins, or other members of the TGF-β family. It is anticipated that OP1 will have specific binding interactions with other "activin-binding" or "bone morphogen-binding" Type II receptors.

The ability of OP-1 to bind to Type I, Type II receptors having binding specificity for activin or BMP-4 but not TGF-B, indicates that OP-1 and OP-1 analogs will be useful as competitors of activin or BMP-4 binding to cell surface receptors. In particular, OP-1 and OP-1 analogs will be useful for competing with activin-ALK-2 binding and/or activin-ALK-2/ActRII (or other Type II) receptor binding; and for competing with BMP-4 (or BMP-2)-ALK-6 binding, and/or BMP-2/BMP-4 ALK-6/daf 4 (or other Type II) binding. The OP-1 competitors may act as antagonists (e.g., binding competitors unable to induce the signal transduction cascade upon binding) or as agonists (e.g., able both to bind and induce the signal transduction cascade).

8.2 IDENTIFICATION OF OP-1 SPECIFIC RECEPTORS IN NONTRANSFECTED CELLS

ALK-5 has been shown to bind TGF-β1, and ALKs 2, 4 bind activin A with high affinities in nontransfected cells (*ten Dijke, Oncogene,* (1993—*Science,* (1994) referenced herein above.) In the present experiment, the binding affinity of OP-1 and/or BMP-4 to receptors in nontransfected cells was demonstrated as follows. The results corroborate the transfected cell data, verifying that OP1 interacts specifically with ALK-2, ALK-3 and ALK-6, but not ALK-4 or ALK-5.

MC3T3-E1 osteoblasts are well characterized cells known to respond to OP-1 and BMP-4 in the induction of alkaline phosphatase activity (Paralkar (1991) *PNAS* 8: 3397–3401.) These cells were affinity labeled using $^{125}$I-OP-1 as described herein above, and cross-linked complexes of about 75 kDa were seen, which were immunoprecipitated only with the ALK-2 antiserum. Tera-2 teratocarcinoma cells and Mv1Lu cells responded to OP-1 as measured by production of plasminogen activator inhibitor-1 (PAI-1). Similar to MC3T3-E1 cells, cross-linked complexes using $^{125}$I-OP-1 in Tera-2 teratocarcinoma were immunoprecipitated only by the ALK-2 antiserum.

On the other hand, cross-linked complexes using $^{125}$I-OP-1 to Mv1Lu cells were immunoprecipitated by ALK-2 as well as ALK-3 and ALK-6 antisera. Mv1Lu cells are known to express ALK-4 and ALK-5 (Ebner (1993) *Science* 260:1344–1348), but cross-linked complexes with 125I-OP-1 were not precipitated by antisera against these receptors. Similarly, cross-linked complexes in U-1240 MG glioblastoma cells were immunoprecipitated by ALK-2 and ALK-6 antisera, and weakly by ALK-3 antiserum. In contrast, cross-linking of 125I-OP-1 to AG1518 human foreskin fibroblasts yielded weak immunoprecipitated components only by ALK-3 antiserum. Type II receptor-like components of about 95 kDa as well as high molecular weight complexes of 140–250 kDa co-immunoprecipitated with certain ALKs in the Tera-2 cells, Mv1Lu cells and U-1240 MG cells.

Receptors for BMP-4 have also been investigated using nontransfected cells. Cross-linked complexes using $^{125}$I-BMP-4 to MC3T3-E1 cells and AG1518 human foreskin fibroblasts were immunoprecipitated only by ALK-3. On the other hand, cross-linking of $^{125}$I-BMP-4 to Tera-2 cells did not yield any immunoprecipitated components by antisera against ALKs.

125I-OP-1 and/or $^{125}$I-BMP-4 also were demonstrated by affinity cross-linking to interact specifically with receptors in other BMP-responsive cells, e.g., MG-63 osteosarcoma cells and PC12 pheochromocytoma cells. A summary of the binding of ALKs to OP-1 or BMP-4 in different cell types is shown in Table II, below. In the Table, "N/T" means not tested, and receptors presented in brackets indicate comparatively lower quantities of radioactive complexes detected.

TABLE II

| Cell lines | Binding of OP-1 | Binding of BMP-4 |
| --- | --- | --- |
| Mouse osteoblasts (MC3T3-E1) | ALK-2 | ALK-3 |
| Mink lung epithelial cells (Mv1Lu) | ALK-2, -3, -6 | N/T |
| Human glioblastoma | ALK2, [-3], -6 | N/T |
| Human teratocarcinoma (Tera-2) | ALK2 | — |
| Human foreskin fibroblasts (AG1518) | [ALK3] | ALK3 |
| Rat osteosarcoma (ROS17/2.8) | ALK2, [-3] | N/T. |

EXAMPLE 9

OP-1, OP-1-SPECIFIC RECEPTOR ANALOG SCREENING ASSAYS

The present invention is useful to determine whether a ligand, such as a known or putative drug, is capable of binding to and/or activating an OP1-specific cell surface receptor as described herein. Ligands capable of specific binding interaction with a given OP-1-specific receptor (e.g., ALK-2, ALK-3, ALK-6) are referred to herein as OP-1 analogs and can be used for therapeutic and diagnostic applications. Some analogs will have the ability to stimulate morphogenetic activity in the cell, mimicking both the receptor binding and signal transducing activity of OP-1. These are referred to OP1 agonists or mimetics. Others will have strong binding affinity but will not stimulate morphogenesis, these are OP-1 antagonists. The analogs can be amino acid-based, or they can be composed of non-proteinaceous chemical structures.

The methods and kits described below similarly can be used to identify OP-1-specific receptor analogs, capable of mimicking the binding affinity of ALK-2, ALK-3 or ALK-6 for OP-1. The analogs can be provided to a mammal to interact with serum-soluble OPI, effectively sequestering the protein and modulating its availability for cell surface interaction.

Transfection of an isolated clone encoding a morphogen receptor into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and compete with the binding of known morphogens, which are labeled by radioactive, enzymatic, spectroscopic or other reagents. Membrane preparations containing the receptor and isolated from transfected cells are also useful in these competitive binding assays. Alternatively, and currently preferred, purified receptor molecules or their ligand binding extracellular domains can be plated onto a microtiter well surface, in a modification of a sandwich assay, e.g., as a competition assay, such as an RIA, described above. Finally, as described above, solution assays, and using only the receptor extracellular domain, also may be used to advantage in these assays. Functional assays of second messenger systems or their sequelae in transfection systems act as assays for binding affinity and efficacy in the activation of receptor function or efficacy in the antagonism of receptor function. Such a transfection system constitutes a "drug discovery system", useful for the identification of natural or synthetic compounds with potential for drug development that can be further modified or used directly as therapeutic compounds to activate or inhibit the natural functions of the receptor encoded by the isolated DNA molecule.

Once such candidate drugs (e.g., OP-1 or receptor-binding analogs thereof) are identified, they can be produced in reasonable, useful quantities using standard methodologies known in the art. Amino acid-based molecules can be encoded by synthetic nucleic acid molecules, and expressed in a recombinant expression system as described herein above or in the art. Alternatively, such molecules can be chemically synthesized, e.g., by means of an automated peptide synthesizer, for example. Non-amino acid-based molecules can be produced by standard organic chemical synthesis procedures. Where the candidate molecule is of undetermined structure, or composition, its composition readily can be determined by, for example, mass spectroscopy. Two approaches to identifying analogs typically are practiced in the art: high flux screens and rational design of ligand mimetics. High flux screens typically screen naturally sourced materials or chemical banks for their ability to bind a protein of interest, here, e.g., the receptor. Typically, compounds are obtained from a range of sources, e.g., chemical banks, microbial broths, plant and animal extracts, and the like. In a high flux screen typically, purified receptor, preferably the soluble, ligand binding extracellular domain, is plated onto a microtiter well surface and a standard volume of a sample solution to be tested then is added. Also added is a standard volume having a known quantity of a purified ligand known to bind the receptor with specificity. Preferably the ligand is labelled with a substance that is readily detectable by automated means (e.g., radiolabel, chromophoric, fluorometric, enzymatic or spectroscopic label.) The wells then are washed and the amount of label remaining after washing or the amount of label remaining associated with the receptor then is detected. Positive scores are identified by the ability of the test substance to prevent interaction of the labelled ligand with the receptor. The screening assays can be performed without undue experimentation, using standard molecular and cell biology tools in common use in the art. For example, screening assays can be performed in standard 96-well plates. Fifteen such plates reasonably can be set up at a time to perform multiple screening assays in parallel. Thus, with only 10–11 reiterations of the screening assay 15,625 ($5^6$) compounds can be screened for their binding affinity. Even allowing for a maximum incubation time of 2 hours, all 15,625 compounds reasonably can be assayed in a matter of days.

High flux screens exploit both the high degree of specificity of the labelled ligand for its receptor, as well as high throughput capacity of computer driven robotics and computer handling of data. Candidate analogs identified in this manner, then can be analyzed structurally and this information used to design and to synthesize analogs having enhanced potency, increased duration of action, increased selectivity and reduced side effects. Candidates also can be used in a rational design program as described below. Finally, candidate analogs also can be tested to determine morphogenetic effect, if any, as described below.

The second approach to the identification of analogs uses a rational design approach to create molecules capable of mimicking the binding effect of OP-1 with an OP1-specific receptor. Here the relevant structure for receptor binding is analyzed to identify critical sequences and structures necessary for binding activity and this information can be used to design and synthesize minimal size morphogen analogs. As for candidate compounds in the high flux assay, design candidates can be tested for receptor binding activity as described above. As described above, a candidate sequence can be further modified by, for example standard biological or chemical mutagenesis techniques to create a candidate derivative having, for example, enhanced binding affinity or another preferred characteristic.

Antibodies capable of interacting specifically with the receptor and competing with OP-1 binding also can be used as an analog. Antibodies can be generated as described above.

OP-1 analogs may be evaluated for their ability to mimic OP-1 or to inhibit OP-1 binding (e.g., agonists or antagonists) by monitoring the effect of the analogs on cells bearing an OP-1-specific receptor (e.g., ALK-2, ALK-3 or ALK-6.) OP-1 agonists are anticipated to have utility in any application where tissue morphogenesis is desired, such as in the regeneration of damaged tissue resulting from mechanical or chemical trauma, degenerative diseases, tissue destruction resulting from chronic inflammation, cirrhosis, inflammatory diseases, cancer and the like, and in the regeneration of tissues, organs and limbs. OP-1 antagonists are envisioned to have utility in applications where tissue morphogenesis is to be limited as, for example, in the treatment of malignant transformations including, but not limited to, osteosarcomas and Paget's disease.

Several exemplary systems for assaying the ability of a candidate analog transduce an OP-1-specific signal across the cellular membrane are described below.

9.1 Induction of Osteoblast Differentiation Markers

For example, OP-1 is known to preferentially induce differentiation of progenitor cells, including embryonic mesenchymal cells and primary osteoblasts (see, for example, PCT US92/07432) As one example, OP-1 analogs can be tested for their ability to induce differentiation of primary osteoblasts, by measuring the ability of these analogs to induce production of alkaline phosphatase, PTH-mediated cAMP and osteocalcin, all of which are induced when primary osteoblasts are exposed to OP-1, 60A or DPP.

Briefly, the assays may be performed as follows. In this and all examples involving osteoblast cultures, rat osteoblast-enriched primary cultures preferably are used. Although these cultures are heterogeneous in that the individual cells are at different stages of differentiation, these cultures are believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, MA), following standard procedures, such as are described, for example, in Wong et al., (1975) PNAS 72:3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that the cells are in serum-deprived growth medium at the time of the experiment.

Alkaline Phosphatase Induction of Osteoblasts

The cultured cells in serum-free medium are incubated with OP1, OP1 analog or a negative control, using a range of concentrations. For example, 0.1, 1.0, 10.0, 40.0 or 80.0 ng OP-1/ml medium typically are used. 72 hours after the incubation period the cell layer is extracted with 0.5 ml of 1% Triton X-100. The resultant cell extract then, is centrifuged, and 100 ml of the extract is added to 90 ml of paranitrosophenylphospate (PNPP)/glycerine mixture and incubated for 30 minutes in a 37° C. water bath and the reaction stopped with 100 ml NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the Biorad method. Alkaline phosphatase activity is calculated in units/mg protein, where 1 unit=1 nmol p-nitrophenol liberated/30 minutes at 37° C. OP-1 induces a five-fold increase in the specific activity of alkaline phosphate by this method. Agonists are expected to have similar induction effects. Antagonists should inhibit or otherwise interfere with OP-1 binding, and diminished alkaline phophatase induction should result when the assay is performed with an antagonist in the presence of a limiting amount of OP-1.

Induction of PTH-Mediated cAMP

The effect of a morphogen analog on parathyroid hormone-mediated cAMP production in rat osteoblasts in vitro may be demonstrated as follows.

Rat osteoblasts are prepared and cultured in a multiwell plate as described above. The cultured cells then are divided into three groups: (1) wells which receive, for example, 1.0, 10.0 and 40.0 ng OP-1/ml medium); (2) wells which receive the candidate analog at various concentration ranges; and (3) a control group which receives no additional factors. The plate is then incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Illinois). OP-1 doubles cAMP production in the presence of PTH. Agonists are expected to have similar induction effects. Antagonists are expected to inhibit or otherwise interfere with OP-1 binding, and diminished cAMP production should result when the assay is performed with an antagonist in the presence of limiting the amount of OP-1.

Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate morphogenic efficacy in vitro.

Rat osteoblasts are prepared and cultured in a multi-well plate as above. In this experiment the medium is supplemented with 10% FBS, and on day 2, cells are fed with fresh medium supplemented with fresh 10 mM b-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP1 or OP-1 analog then is added to the wells directly, e.g., in 50% acetonitrile (or 50% ethanol) containing 0.1% trifluoroacetic acid (TFA), at no more than 5 ml OP-1/ml medium. Control wells receive solvent vehicle only. The cells then are re-fed and the conditioned medium sample diluted 1:1 in standard radioimmunoassay buffer containing standard protease inhibitors and stored at $-20°$ C. until assayed for osteocalcin. Osteocalcin synthesis is measured by standard radioimmunoassay using a commercially available osteocalcin-specific antibody and can be confirmed by Northern blot analysis to calculate the amount of osteocalcin mRNA produced in the presence and absence of OP-1 or OP-1 analog. OP-1 induces a dose-dependent increase in osteocalcin production (5-fold increase using 25 ng of OP-1 protein/ml), and a 20-fold increase in osteocalcin mRNA. Agonists are expected to have similar induction effects; antagonists are expected to inhibit or otherwise interfere with OP-1 binding, thereby substantially interfering with osteocalcin induction in the presence of a limiting amount of OP-1.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture. OP-1 induces a 20-fold increase in initial mineralization rate. Agonists are expected to have similar induction effects; antagonists are expected to inhibit or otherwise interfere with OP-1 binding, thereby inhibiting mineralization induction in the presence of a limiting amount of OP-1.

9.2 Induction of a Constructed Reporter Gene

Alternatively, a reporter gene construct can be used to determine the ability of candidate molecule to induce signal transduction across a membrane following receptor binding. For example, PAI-1 protein, (Plasminogen Activator Inhibitor-1) expression can be induced by OP-1 in Mv1Lu-cells (see above). Also, as demontrated above, these cells express ALK-2, -3 and -6 surface receptors. In addition, preliminary studies indicate that ALK-1, when overexpressed in a chemically mutagenized derivative of these cells, also apparently mediates PAI-1 induction in the presence of OP-1.

Accordingly, PAI-1 promoter elements can be fused to a reporter gene and induction of the reporter gene monitored following incubation of the transfected cell with a candidate analog. As one example, the luciferase reporter gene can be used, in, for example, the construct p3TP-Lux described by Wrana et al. (1992) Cell 71: 1003–1014 and Attisano et al. (1993) Cell 74: 671–680. This reporter gene construct includes a region of the human PAI-1 gene promoter in combination with three sets of tetradecanoyl phorbol-acetate responsive elements upstream of the lucifrase open reading frame.

In a typical assay, transfected cells starved in DMEM containing 0.1% fetal bovine serum and antibiotics (e.g., 100 units/ml penicillin and 50 $\mu$/ml streptomycin) for 6 hrs., and then exposed to ligand for 24 hr. Luciferase activity in the cell lysate then is measured using a luminometer in the luciferase assay system, according to the manufacturer's protocol(Promega). In Mv1Lu mutant cells, "R mutant" cells co-transfected with ALK-2 and Act RII, OP-1 mediated induction of luciferase activity.

9.3 Inhibition of Epithelial cell proliferation

OP-1 is known to inhibit epithelial cells. Thus, the ability of a candidate analog to inhibit cell proliferation, as measured by $^3$H-thymidine uptake by an epithelial cell can be used in an assay to evaluate signal transduction activity of the candidate. Analogs competent to inhibit epithelial cell growth are contemplated to have particular utility in therapeutic applications where limitation of a proliferating cell population is desired. Such applications include chemotherapies and radiation therapies where limiting the growth of a normally proliferating population of cells can protect these cells from the cytotoxic effects of these cancer therapies. (see e.g., WO94/06420). In addition, psoriasis and other tissue disorders resulting from uncontrolled cell proliferation, including benign and malignant neoplasties, can be modulated by use of an OP-1 analog.

As an example, mink lung epithelial cell growth is inhibited by OP-1. (see, PCT US93/08885; WO94/06420.) As described above, derivatives of these cells [e.g., "R-4 mutants", clone 4–2, Laiho et al. (1990) J. Eiol. Chem. 265: 18518–18524] can be transfected with DNA encoding OP-1-specific receptors and induced to express these receptors. The transfected cells, then can be assayed for a candidate analog's ability to block cell growth. As one example, when R-4 cells are transfected with ALK-3 under a $Zn^{2+}$-inducible promoter, and induced to express the receptor following induction with $ZnCl_2$, cell growth can be inhibited in the presence of OP-1 in a dose dependent manner. Preliminary experiments with ALK-1 indicates that this receptor also can mediate this OP-1-specific effect.

In a typical assay, cells are seeded in 24-well cell culture plates at a density of $10^4$ cells per well in DMEM with 10% FBS, and incubated overnight. The medium is replaced with DMEM containing 0.2% FBS and 100 uM $ZnLC_2$, and the cells are incubated for 5 h, after which the medium is replaced with fresh DMEM containing 0.2% FBS, 100 uM $ZnCL_2$ and various concentrations of OP-1 or an analog candidate. After 16 h of incubation, 0.25 ci of [$^3$H]thymidine (Amersham) are added and the cells incubated for an additional 2 h. Thereafter, the cells are fixed in 10% trichloroacetic acid for more than 15 min on ice, and solubilized with 1 M NaOH. The cell extracts are neutralized with 1 M HCl and $^3$H radioactivity determined in a liquid scintillation counter.

EXAMPLE 10

SCREENING ASSAY FOR COMPOUNDS WHICH ALTER ENDOGENOUS OP1 RECEPTOR EXPRESSION LEVELS

Candidate compound(s) which can be administered to affect the level of a given endogenous OP-1 receptor can be found using the following screening assay, in which the level of OP1 receptor production by a cell type which produces measurable levels of the receptor is determined by incubating the cell in culture with and without the candidate compound, in order to assess the effects of the compound on the cell. This also can be accomplished by detection of the OP1 receptor either at the protein level by Western blot or immunolocalization, or at the RNA level by Northern blot or in situ hydridization. The protocol is based on a procedure for identifying compounds which alter endogenous levels of OPi expression, a detailed description also may be found in PCT US 92/07359, incorporated herein by reference.

Cell cultures of, for example, bone, brain, intestine, lung, heart, eye, breast, gonads, kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells can be cultured, for example, in Dulbeccols Modified Eagle medium (Gibco, Long Island, NY) containing serum (e.g., fetal calf serum at 1%–10%, Gibco) or in serum-deprived medium, as desired, or in defined medium (e.g., containing insulin, transferrin, glucose, albumin, or other growth factors).

Cell samples for testing the level of OP-1 receptor production are collected periodically and evaluated for receptor production by immunoblot analysis (Sambrook et al., eds., 1989, Molecular Cloning, Cold Spring Harbor Press, Cold Spring Harbor, N.Y.), or, alternatively, a portion of the cell culture itself can be collected periodically and used to prepare polyA+ RNA for mRNA analysis by Northern blot analysis. To monitor de novo receptor synthesis, some cultures are labeled according to conventional procedures with an $^{35}$S-methionine/$^{35}$S-cysteine mixture for 6–24 hours and then evaluated to quantitate receptor synthesis by conventional immunoassay methods. Alternatively, anti-receptor antibodies may be labelled and incubated with the cells or cell lysates, and the bound complexes detected and quantitated by conventional means, such as those described hereinabove. Northern blots may be performed using a portion of the OP-1 receptor coding sequence to create hybridization probes, and following the RNA hybridization protocol described herein.

EXAMPLE 11

GENERAL FORMULATION/ ADMINISTRATION CONSIDERATIONS

The analogs and constructs described herein can be provided to an individual as part of a therapy to enhance, inhibit, or otherwise modulate the in vivo binding interaction between OP-1 and one or more OP1-specific cell surface receptors. The molecules then comprise part of a pharmaceutical composition as described herein below and can be administered by any suitable means, preferably directly or systemically, e.g., parenterally or orally. Where the therapeutic molecule is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the therapeutic preferably comprises part of an aqueous solution. The solution preferably is physiologically acceptable so that in addition to delivery of the desired morphogen to the patient, the solution does not otherwise adversely affect the patient's electrolyte and volume balance. The aqueous medium for the therapeutic molecule thus may comprise normal physiologic saline (0.9% NaCl, 0.15M), pH 7–7.4 or other pharmaceutically acceptable salts thereof.

Useful solutions for oral or parenteral administration can be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen in vivo.

Other potentially useful parenteral delivery systems for these therapeutic molecules include ethylene-vinyl acetate copolymer particles, osmotic pumps, implantable infusion systems, and liposomes. Formulations for inhalation administration may contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally.

Alternatively, the morphogens described herein may be administered orally.

The therapeutic molecules also can be associated with means for targeting the therapeutic to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting therapeutics to bone tissue. Alternatively, an antibody or other binding protein that interacts specifically with a surface molecule on the desired target tissue cells also can be used. Such targeting molecules further can be covalently associated to the therapeutic molecule e.g., by chemical crosslinking, or by using standard genetic engineering means to create, for example, an acid labile bond such as an Asp-Pro linkage. Useful targeting molecules can be designed, for example, using the single chain binding site technology disclosed, for example, in U.S. Pat. No. 5,091,513.

Finally, therapeutic molecules can be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents and analgesics and anesthetics.

Therapeutic molecules further can be formulated into pharmaceutical compositions by admixture with pharmaceutically acceptable nontoxic excipients and carriers. As noted above, such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275, the disclosure of which is incorporated herein by reference. The composition then can be painted, sprayed or otherwise applied to the desired tissue surface.

The compositions can be formulated for parenteral or oral administration to humans or other mammals in therapeutically effective amounts, e.g., amounts which provide appropriate concentrations of the analog to target tissue for a time sufficient to induce the desired effect.

Where the analog is to be used as part of a transplant procedure, it can be provided to the living tissue or organ to be transplanted prior to removal of tissue or organ from the donor. The analog may be provided to the donor host directly, as by injection of a formulation comprising the analog into the tissue, or indirectly, e.g., by oral or parenteral administration, using any of the means described above.

Alternatively or, in addition, once removed from the donor, the organ or living tissue can be placed in a preservation solution containing the therapeutic molecule. In addition, the recipient also preferably is provided with the analog just prior to, or concomitant with, transplantation. In all cases, the analog can be administered directly to the tissue at risk, as by injection to the tissue, or it may be provided systemically, either by oral or parenteral administration, using any of the methods and formulations described herein and/or known in the art Where the therapeutic molecule comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell,(solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components can be found, for example, in U.S. Pat. No. 5,002,965, the disclosure of which is incorporated herein by reference.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to and individual where typical dose ranges are from about 10 ng/kg to about 1 g/kg of body weight per day; a preferred dose range being from about 0.1 mg/kg to 100 mg/kg of body weight. No obvious morphogeninduced pathological lesions are induced when mature morphogen (e.g., OP-1, 20 mg) is administered daily to normal growing rats for 21 consecutive days. Moreover, 10 mg systemic injections of morphogen (e.g., OP-1) injected daily for 10 days into normal newborn mice does not produce any gross abnormalities.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for identifying an OP-1 analog having the same binding affinity for a cell surface receptor as OP-1, the method comprising the steps of:
   (a) providing a sample comprising cells flat express a surface receptor having binding specificity foe OP-1, said receptor selected from the group consisting of:
      (i) a polypeptide comprising amino acid residues 16–123 of SEQ ID NO: 4 (ALK-2);
      (ii) a polypeptide comprising amino acid residues 24–152 of SEQ ID NO: 6 (ALK-3);
      (iii) a polypeptide comprising amino acid residues 23–122 of SEQ ID NO: 8 (ALK-6); and
      (iv) a polypeptide having binding affinity for OP-1 and encoded by nucleic acids 256–552 of SEQ ID NO: 7 (ALK-6);
   (b) contacting said sample with a candidate OP-1 analog; and
   (c) detecting binding affinity of said candidate to an OP-1 cell surface receptor;
   wherein an OP-1 analog is identified as a candidate having the samed binding affinity for said receptor as OP-1.

2. The mnethod of claim 1 wherein said receptor comprises an intracellular kinase domain.

3. The method of claim 2 wherein said OP-1 mediated cellular response comprises induction of a kinase activity.

4. The method of claim 1 wherein said cells further express part or all of a Type II serine/threonine kinase receptor having binding affinity for OP-1, activin or BMP-4.

5. A kit for identifying OP-1 or a candidate OP-1 analog in a sample, the kit comprising:
   (a) a receptacle adapted to receive a sample and containing a receptor selected from the group consisting of:
      (i) a polypeptide comprising amino acid residues 16–123 of SEQ ID NO: 4 (ALK-2);
      (ii) a polypeptide comprising amino acid residues 24–152 of SEQ ID NO: 6 (ALK-3);
      (iii) a polypeptide comprising amino acid residues 23–122 of SEQ ID NO: 8 (ALK-6); and
      (iv) a polypeptide having binding affinity for OP-1 and encoded by nucleic acids 256–552 of SEQ ID NO: 7 (ALK-6);
   (b) a separate receptacle containing a molecule selected from the group consisting of: OP-1 and BMP-4.

6. The kit of claim 5 further comprising a serine/threonine Type II receptor having binding specificity for OP-1, activin or BMP-4.

* * * * *

UNITED STATES PATENT AND TRADEMARK OFFICE
CERTIFICATE OF CORRECTION

PATENT NO. : 6,632,618 B1
DATED : October 14, 2003
INVENTOR(S) : Peter T. Dijke

It is certified that error appears in the above-identified patent and that said Letters Patent is hereby corrected as shown below:

<u>Title page,</u>
Item [73], Assignee, delete "Curtis, Inc." and insert -- Curis, Inc. --

<u>Column 1,</u>
Line 5, insert -- a continuation of PCT/US95/05467, filed April 28, 1995, which is -- after "This application is" and before "a Continuation-In-Part."

<u>Column 75,</u>
Line 55, replace "samed" with -- same --.

<u>Column 76,</u>
Line 33, delete beginning with "3. The method of" to and including "kinase activity."
Line 34, insert the following claim:

3. The method of claim 2 wherein said cells are transfected with a nucleic acid comprising a reporter gene in operative association with a control element, said control element inducible by an OP-1 analog.

Signed and Sealed this

Tenth Day of February, 2004

JON W. DUDAS
*Acting Director of the United States Patent and Trademark Office*